United States Patent [19]
Bergsma et al.

[11] Patent Number: 5,830,649
[45] Date of Patent: Nov. 3, 1998

[54] HUMAN GALACTOKINASE GENE

[75] Inventors: Derk Jon Bergsma, Berwyn, Pa.; Dwight Edward Stambolian, Martlon, N.J.

[73] Assignee: SmithKline Beecham Corporation, Philadelphia, Pa.

[21] Appl. No.: 451,778

[22] Filed: May 26, 1995

Related U.S. Application Data

[63] Continuation-in-part of PCT/US94/10825, Sep. 23, 1994.
[51] Int. Cl.$^6$ .............................. C12Q 1/68; C07H 21/00; C12N 15/12; C12N 15/55
[52] U.S. Cl. ........................... 435/6; 435/69.1; 435/91.41
[58] Field of Search ............................ 435/6, 69.1, 91.41; 536/23.1, 23.2, 23.5, 24.3

[56] References Cited

PUBLICATIONS

Stambolian, et al., "Purification of Human Galactokinase and Evidence For Its Existence as a Monomer Form", (1985), *Biochimica Biophysica Acta*, 831:306–312.

Lee et al., "Cloning of a Human Galactokinase Gene (GK2) on Chromosome 15 By Complementation in Yeast", (1992), *Proc. Natl. Acad. Sci, USA*, 89:10887–10891.

Debouck, et al., "Structure of the Galactokinase Gene of *Escherichia coli*, the Last (?) Gene of the gal Operon", (1985), *Nucl. Acids Research*, 13:1841–1853.

Glaser, et al., "*Bacillus subtilis* Genome Project: Cloning and Sequencing of the 97 kb Region From 325° to 333°", (1993), *Molecular Microbiology*, 10:371–384.

Houng, et al., "Molecular Cloning and Physical and Functional Characterization of the *Salmonella typhimurium* and *Salmonella typhi* Galactose Utilization Operons", (1990), *Journal of Bacteriology*, 172:4392–4398.

*Primary Examiner*—Jasemine C. Chambers
*Assistant Examiner*—Scott D. Priebe
*Attorney, Agent, or Firm*—Alissa M. Eagle; William T. King

[57] ABSTRACT

This invention relates to human galactokinase and the identification of galactokinase mutations, a missense and nonsense, as well as isolated nucleic acids encoding same, recombinant host cell transformed with DNA encoding such proteins and to uses of the expressed proteins and nucleic acid sequences in therapeutic and diagnostic applications.

34 Claims, 5 Drawing Sheets

```
5'
CCGAGCATCCCGCGCCGACGGGTCTGTGCCGGAGCAGCTGTGCAGAGCTGCAGGCGCGCG    -3
TCATGGCTGCTTTGAGACAGCCCCAGGTCGCGGAGCTGCTGGCCGAGGCCCGGCGAGCCT    58
   M  A  A  L  R  Q  P  Q  V  A  E  L  L  A  E  A  R  R  A

TCCGGGAGGAGTTCGGGGCCGAGCCCGAGCTGGCCGTGTCAGCGCCGGGCCGCGTCAACC    118
 F  R  E  E  F  G  A  E  P  E  L  A  V  S  A  P  G  R  V  N

TCATCGGGGAACACACGGACTACAACCAGGGCCTGGTGCTGCCTATGGTGAGGGGCTGCA    178
 L  I  G  E  H  T  D  Y  N  Q  G  L  V  L  P  M

CGGGGAGCCCCTAGCCCGCCGCCGCCTGTCCCGGTCGCCGAGGAGGGCGGGCCTCGGGGA    238
CGCTGGGGGCGAGTTCTTCCCGCGGGAGATGTGGGGCGGGCAGCTGCGCCTGGAGCACCG    298
GTGCACGGAAGAGTCCCCGGGACAGGCTGTTCCCCACGTTGGAAGGGAGGAAGCGAAGAA    358
GTGGTCCCCAGAGGGTGCGCGGCCGCCTCTTGGCTCAAGCCCGCCCTCTGGGGGCTGGGG    418
CTCCTCGCCTTCAACCTGGGAGCATGTTCCCCTTAAACTGTGAGGCCCTGTGTGCCACGC    478
AGAAGGGGACACTCCGCGCCTCCGGCCACCGTGGGGCCCCAACCGCAGACCTGGGCGAAC    538
GTAGCCTTCTGGCCCAGCCCGTTCAATTTACAGAGGAGGAAACTGAGGCCTAGAGAGGCC    598
CAGTGAACTGCTGGAGGTCACACAGCAGGTTCTTGGCGGGGCTGCGACTTGGGAGTGAGG    658
ACCCCAGCTTTCAGCGGGGGCGCTTTCCGCCCCATCTGCAGCTTGGGGAGTGCACAGG     718
TACAGGATGTCCAGAGCCACCCAAAATGTAAAGGCTTTGGAGCTCCAGTGATCTGTTTTC    778
CCTTTGGGCTAAGCTCTCCCCCCTTGCCCCACAGCTCAGGGCAGAGTCCAGGTCTGTGCT    838
CCAGCTGCAGCCGCCCCGCCCCTGAAGACCTAAGGGGGCAGGGCTCAAGCCCCCAAGGTC    898
AGCTGGCCCTCAGGATCTTCCCTGCGACGCTGAACCTGGAGGTTCAGAACCTGATGACTG    958
TGGAGGCATCAGAACCTCGGCTGGAGGCAGTGTCATTGGAGAGGCTTACTCCAGCTGGCG    1018
GAAGCCTCACGTACTGCTTGTCTCTCCTGCCAGGCTCTGGAGCTCATGACGGTGCTGGTG    1078
                                       A  L  E  L  M  T  V  L  V

GGCAGCCCCCGCAAGGATGGGCTGGTGTCTCTCCTCACCACCTCTGAGGGTGCCGATGAG    1138
 G  S  P  R  K  D  G  L  V  S  L  L  T  T  S  E  G  A  D  E

CCCCAGCGGCTGCAGTTTCCACTGCCCACAGCCCAGCGCTCGCTGGAGCCTGGGACTCCT    1198
 P  Q  R  L  Q  F  P  L  P  T  A  Q  R  S  L  E  P  G  T  P

CGGTGGGCCAACTATGTCAAGGGAGTGATTCAGTACTACCCAGGTATGGGGCCCAGGCCT    1258
 R  W  A  N  Y  V  K  G  V  I  Q  Y  Y  P

GAGCCAAGTCCTCACTGATACTAGGAGTGCCACCTCACAGCCACAGAGCCCATTCATTTG    1318
TCTGATACACTGTGGGGAAGGCTTGTAGAGTGGAGCATCCCATTGTACAGATGAGGAAAC    1378
TGATGCCCCAGAAGGTCGGGAACTTGCCCTGGGTTTCCCGTGACCTGATTGGAGGAGCC    1438
AGGATTTGAACCCCAGCCTTTTTTCCCTCCAGAGCCCTAAACCAGGAGGACAATTAGAAG    1489
TGTCCCAGCAACCTCAGAGGGTGGGAAAATGGAGGGGAGTGGGTCCCTTGGGCCAGCAGG    1558
TTGGTGGGGTTCTTGACAATTGAGACACACACCTAGAAACAGTTGCTAGGCCGTTGCTGC    1618
CCTTCCCGCCAGGACACCTGCCCTTCCTGTCCAATCCTCCCAGGCAGCCTCTCTTACCAT    1678
CACCTGTTCTTTCCCCCTGCAGCTGCCCCCCTCCCTGGCTTCAGTGCAGTGGTGGTCAGC    1738
                                A  A  P  L  P  G  F  S  A  V  V  V  S

TCAGTGCCCCTGGGGGGTGGCCTGTCCAGCTCAGCATCCTTGGAAGTGGCCACGTACACC    1798
 S  V  P  L  G  G  G  L  S  S  S  A  S  L  E  V  A  T  Y  T

TTCCTCCAGCAGCTCTGTCCAGGTACCAGCTAGGCCCCAGCCCTGACCCAGCCCTCCTTC    1858
 F  L  Q  Q  L  C  P
```

FIG. 2A

```
CCTGAGGTCTCCAGGTGGTCCCAGCTTCTACTATGCCTTATGGAGGGGGTGGCAGGGAAT    1918
CTCCCTGGAGTGTCATTGAAGCCACTGCTGCTTCCACCAGCCCTAGCCTCCCCACCTCAC    1978
CCTGTACTGCAGACTCGGGCACAATAGCTGCCCGCGCCCAGGTGTGTCAGCAGGCCGAGC    2038
         D  S  G  T  I  A  A  R  A  Q  V  C  Q  Q  A  E

ACAGCTTCGCAGGGATGCCCTGTGGCATCATGGACCAGTTCATCTCACTTATGGGACAGA    2098
 H  S  F  A  G  M  P  C  G  I  M  D  Q  F  I  S  L  M  G  Q

AAGGCCACGCGCTGCTCATTGACTGCAGGTTGGGCTCGCTCCCCTCGTCCCCTCCCGCCC    2158
 K  G  H  A  L  L  I  D  C  R

TGCACTCAGCAGCTCCTGGGTGGAGTGTGCCCACTGCCTGGCGCAGCAAGCACACGCTTG    2218
GCCTCGTCATCTCCCCCATTGTAACTCCACCCCAGGTCCTTGGAGACCAGCCTGGTGCCA    2278
                                        S  L  E  T  S  L  V  P

CTCTCGGACCCCAAGCTGGCCGTGCTCATCACCAACTCTAATGTCCGCCACTCCCTGGCC    2338
 L  S  D  P  K  L  A  V  L  I  T  N  S  N  V  R  H  S  L  A

TCCAGCGAGTACCCTGTGCGGCGGCGCCAATGTGAAGAAGTGGCCCGGGCGCTGGGCAAG    2398
 S  S  E  Y  P  V  R  R  R  Q  C  E  E  V  A  R  A  L  G  K

GAAAGCCTCCGGGAGGTACAACTGGAAGAGCTAGAGGGTGAGAACTGCCAGGGTGCTCTA    2458
 E  S  L  R  E  V  Q  L  E  E  L  E

TCCTGGAGGCGGCTGTGCTCCCTGCTGGCGCCTCAGTGTGGCCTTGACCCTGCCTGGGAC    2518
CCCGATCTCCAGGGGCTTCTGCCATGCTCTCCCCAGTCCCTTCAAACACTGCGCACCCAG    2578
GGTTCCAATCTCAGCAGGGGTGCTTGAAATCCTAAAATGGTCTTATCTAATCAGAAAAAT    2638
CATGTTTCCATTGTGGAAAATGTAGAAAAGTACAAAGTAGAAAATAATAAGCTATAAGGG    2698
CACTACCCAGAGATAGGCACTGCTGACATTTTCACGTTTCCTTTCAGTATTTTTCCACAT    2758
CTGTCTTCAAAGCTGAGTATATGTAATATATCATCACTTTCCCCCCCCACCCCCTTTTTT    2818
TTAAGAGGCAGGGTCTCATTCTGTTGCCCAAGCTGGAGTGTAGTGGTGTGATCATAGCTT    2878
ACTGCAAACTTGAACTCTTGAGCTCAAGGGATCCTCCCAGCTCAGCCTTCCAAGTAGCTG    2938
AGATTACAGGTGTGCCACCATGCCCGGCTAATTTTTATCTTCGTAAAGACGGCCTTGTAG    2998
TGTTGCCCAGGATGATCCTGAACTCTGGCCTCAAGAGGTCCTCCTGCCTTGGGCTCCCAA    3058
AGTGTTGGGATTATAGGCATGAGCCACTGCGGCCAGCCCATTTGCCGTGTTTTTTTTTTG    3118
GACACAGAGTTTCGGTCTTGTCACCCATGCTGGAGTGCAATGGTGCGATCTCAGCTCACT    3178
GTAACCTCTGCCTCCCGGGTTCAAGTGATTCTCCTGCCTCAGCCTCCCGAGTAGCTGGGA    3238
CTACAGGCGCCCGCCACTACGCCTGGCACATTTTTTATAGTTCTAGTAGAGACTGGGGTT    3298
TCACCATGTTGGCCAGGCTGGTCTCAAACGCCTGACCTCAGGTGATCCTCCCGCCTCAGC    3358
CTTCCAAAGTGCTGGGATTACAGGCGTGAGCCATAGTGCCGGTCTCTTTTTTTTTTTTTT    3418
TTAAACTAAACATAATCTCAGAACCCAGAACCCTATCTTATCTTATGCCATGAAAGGCAT    3478
ATCTCGGCGTGGCTCTTTTTTTTTTTTTTTCTTTTTTTTTGGGCGAGGTGGAGGCTTGCC    3538
CTGTTGCCCAGGCTGGAGTGCAGCGGCGCAATCTCGGTTCACTGCATCCTCCACCTCCTG    3598
GGTCCAAATGATCCTCCTGCCTTAGCTTCCTGAGTAGGTGGGATTACTGGAACCCACCAC    3658
CACGCCCAGCCAATTTTTATATTTTTAGTAGAGACGGGGTTTCATGTTGGCCAGGCTGGC    3718
CTCGAACTCCTGACCTCGTGATCTGCCCGCCTCAGCCTCCCAATGTGCTAGGATTACATG    3778
TGTGAGCCACTGCACCTGGCCTCCGTGTGGCTCTTTAAAGCTCCACAATATTTTAGCATT    3838
CAGGTGCTCTGTCATTTACTTAACTATTTTCTGATACACCTCACACTGCGATTAACTTTC    3898
CTTATTTATCTTTTTTATTATTTATTTATTTATTTGAGACAGAGTCTTGCTCTGTC       3958
ACCCAGGCTGGAGTGCAGTGGCACGATCTCGGCTCACTGCAACCTCTGCCTCCCAGGTTC    4018
AAGTGATTCTCCTGCCTCAGCCTCCTGAGTAGCTAGGATTAGAGGCATGTGCCACCACAC    4078
CTGGCTAATCTTCGTATTTTTAGCAGAGATGAGGTTTTACCATGTTGGTCGGGCTGGTCG    4138
```

FIG. 2B

```
TGAACTCCTGACCTGGTGATCTGCCCACCTCAGCCTCCCAAAGTACTGGGATGACAGGCA  4198
TGAACCACTGTGCCTGGCCATCTTTTTTATTTTTTAAAGAGATGGGTTCTGCTAAGTTGC  4258
CCAGGCTGGACCTGAACTCTTGGGCTCAAGTAATCTTCTCACCTAGTCTCCTGGGTAGCT  4318
GCAACCAAAGGCACCCGGTTTATCTGCATTCTCTTTTTTTTCTTTGAGACTGAGTCTTGC  4378
TCTGTAGCCCAGGCTGGAGCGCAGTGGCGTGATCTCGGCTCACTGCAACCTCCGTCTTCA  4438
GGGTTCAAGCAATTCTCCTGCCTCAGCCTCTGGAGTGGCTGGGACTACAGGCGTGTGCCA  4498
CCAGAGCGAGTTAATTTTTTTTTTTTTGTATTTTTAGTGGACACTGGGTTTCACTATA    4558
TTGGCCAGGCTGGTCTTGGACTCCTGACCTCAAGTGATCCGCCTGCCTTGGCCTCCCAAA  4618
GTGCTGGGATTACAGGCACAGGCGTGAGCCACTACACCTGGCCTATCTGCATTCTCTTAA  4678
TAGTTTCTTAGAAATGGATTCTTAGGAGTAGGATTACAGAGTCAAGAGACACAAGTTTTG  4738
TAGGCTGGGTGCGGTGGCTCACGTCTGTGCCTGTAATCCCAGTACTTTAGGAGGCCAAGG  4798
TGGGCAGATTCATTGAGCTCAGGAATTCGAGACCAGCCTGGGCAACATGGCAAAACCCCA  4858
TCTCTAAAGAAATACAAAAATTAGCCAGGTGTGGTGGTGTGCCTGTAGTCCTAGCTAC    4918
TTAGGAGGCTGGGGTGGGAGGATCAATTGAGCCCAGGAGGTTGAGACTGCAGTGAGCTGT  4978
GATTGCACCATGGCACTCCAGCCTGGGCCTCAAAGTGAGATCCTGTCTCCAAAACAAAAA  5038
AGATACAAGTATCCTTAAGGCTCCTGCTACACATGGCCAGGAAGGTAGTCTATTGGACAG  5098
TTTTAAGGTCATTATCAATATTAGCTCATTTAATTCCCTCCAAAACTCTGTAAAGCACAT  5158
TCTGCTACCATAGTTGTCATATTTTTGATGGGGGAATCTACAGTGAGAGGCAGTGCTGGG  5218
ATCTGAACCCCATCTGGACAGATTAGCTCCAGGGCCCATGCTCTTGACTGGCTGGCCGCG  5278
CTGCCCACACTGAGTTGTTCCTTCCTGGCAGGGTAGGTGTGCCTATCTCAGGGACACTAG  5338
ACAGCTCCGAGGGACCTCCCTGTCCTTTTCCTTTGTGAACTGTGTCACGTTCTCCAGAGC  5398
AGGGCTCAGACCTGCCCTGCCTGCTCTGTGCAGATGCCCTTGGCCAAGGTTTTCACACTG  5458
GAACAAGTTGGTCCCTCCTCCCCACCCCAGCCTGTCCTTGGCCCTCCTCCAGGTCTCCTT  5518
CTGCATAGGAGCAGCTCACCCTGCCTCCTCCAGAGTCCTGCCCTAGAAGCGCAATCCCTC  5578
TCCTTCCATCCCCTGCCTGGCTGCCTGGCTCCTTCCCTCAGCCTCCAAGACATGCTCAGT  5638
TTTCTTCCCTCCTAAAACACCACCCACTGTCTCATTTCCATTCATTTCTTTCTTTCTTTC  5698
TTTCTTTTTTTTTTTTGAGAGGGAGCCTCACTCTGTCACCCAGGCTGAAGTGCAGTGGCA  5758
TGATCTCCACTCACTGCAACCTCCGCCTCCCAGGTTCAAGCAATTCTCCTGCCTCAGCCT  5818
CCTGAGTAGCTGGGATTACAGGCGCCTGCCACGATGCCCGGCTAACTTTTGTATTTTTAG  5878
TAGAGACGGGGTTTCGCCATGTTGGCCAGGCTGGTCTCGAGCTCCTGACCTCAGGCAATC  5938
TGCCTGCCTCAGCTTCCCAAAGTGCTGGGATTACAGGTGTGAGCCACCGCGCCCACCCAT  5998
TCATTTCTCAGTCCTTTGAATCTACTTGCCCCTCCATCCCGCCATGCCACCTACCCTAAC  6058
AACCTTCCCCCTTTAAACCTGCGGGTTTGGCCGGGCGCAGTACACTGAGTCAGTACTGGTA  6118
CTGACCCAGGTACCCCTCCAGCCTCAGCTCCAGTCAGATGGGACAGCCTGCTGGTCCCTG  6178
GCTGCTTCTGCCCCCTCTTCTGGAGCCCCAGCCCTGGAGGCTCCATGTGGCTCAGCAGAA  6238
CTTCTTCTCCTCCTGCTCTGTGGTGGCCTCTTGAGGGCAGCACTCACCTTGGAAAGCATG  6298
GAGTGTTTCAACCCTCACTGCTCCCTGAAGGACCAAGGTGTCCCATTTTACAGTCGGGGG  6358
AGGAGGCACTGTGATAAAGGGGCTCTTCAGACCCACGTCTGAGAGAGCCAGGCTGCGCCG  6418
CCCCCGCGGCCTTCCACCCTTCACCGTCCAGCCAGGGCCACTGCCATCACCGCCTGCTGG  6478
TCCTCACAGGCGTCGGGGCCCCAGGCAGTGAGAAGGCGGCTGCTGACTCCTCTTTCCTCC  6538
CCAGCTGCCAGGGACCTGGTGAGCAAAGAGGGCTTCCGGCGGGCCCGGCACGTGGTGGGG  6598
     A  A  R  D  L  V  S  K  E  G  F  R  R  A  R  H  V  V  G

GAGATTCGGCGCACGGCCCAGGCAGCGGCCGCCCTGAGACGTGGCGACTACAGAGCCTTT  6658
 E  I  R  R  T  A  Q  A  A  A  A  L  R  R  G  D  Y  R  A  F

GGCCGCCTCATGGTGGAGAGCCACCGCTCACTCAGGTGAGGCCCTCTGGGCGCCCCGCTC  6718
 G  R  L  M  V  E  S  H  R  S  L  R

CTGCCGGGCACAGGCCGGCCCAGGCCCACCCCTTCAATATCCTCTCTGCAGAGACGACTA  6778
                                                  D  D  Y
```

FIG. 2C

```
TGAGGTGAGCTGCCCAGAGCTGGACCAGCTGGTGGAGGCTGCGCTTGCTGTGCCTGGGGT    6838
  E  V  S  C  P  E  L  D  Q  L  V  E  A  A  L  A  V  P  G  V

TTATGGCAGCCGCATGACGGGCGGTGGCTTCGGTGGCTGCACGGTGACACTGCTGGAGGC    6898
  Y  G  S  R  M  T  G  G  G  F  G  G  C  T  V  T  L  L  E  A

CTCCGCTGCTCCCCACGCCATGCGGCACATCCAGGTGGGCGGGCACCAGGGCCTGGGCGG    6958
  S  A  A  P  H  A  M  R  H  I  Q

GCAGGAGCGGCAGCTTCCCGGGGCCCTGCCACTCACCCCCAGCCCGCCTCTTACAGGAGC    7018
                                                             E

ACTACGGCGGGACTGCCACCTTCTACCTCTCTCAAGCAGCCGATGGAGCCAAGGTGCTGT    7078
  H  Y  G  G  T  A  T  F  Y  L  S  Q  A  A  D  G  A  K  V  L

GCTTGTGAGGCACCCCCAGGACAGCACACGGTGAGGGTGCGGGGCCTGCAGGCCAGTCCC    7138
  C  L  *

ACGGCTCTGTGCCCGGTGCCATCTTCCATATCCGGGTGCTCAATAAACTTGTGCCTCCAA    7198
TGTGGTACCTGCCTCCTCTAGAGGTGGGTGTATGCTTGGGTGTCAGAGAATGGGGGATGT    7258
CAGAACCGCTCCCCTACCCTAGGGGAGCACCTCTCAGGCCCCAGAAGAATGGGCAAGGCA    7318
GGGCCTAGCAGTAGCAAAACCATTTATTAAGTGCAGAACAAAGGCTGGGTCCTTGTGCTG    7378
CTCCCAGCTCTTTGGTTACAAATAGGTTTGGGCCCACAGAGGACGGACCTTGCCCCCTTC    7438
ATGCCTCCAGGAGACACCTAGCCCCTGCTCTGTGCATGCGGGTGGGCTGGGCCCCCAGG    7498
GGTGCAAGGATGGAGTAGCTGAGGAGGCTCCGGGAGAGGAGTCGGGAGGACGCCTAGTGG    7558
GACATTGCGGGGGTGGCGCAGGGTGCGGTCAAGTTTGGAAGAAACTGTTGGGTCCA      7614
                                                         3'
```

FIG. 2D

HUMAN GALACTOKINASE GENE

This invention was made in part with government support under EY-09404 awarded by the National Institutes of Health. The U.S. Government has certain rights in the invention.

CROSS-REFERENCE TO RELATED APPLICATIONS

This application is a continuation-in-part of application PCT/US94/10825, filed 23 Sep., 1994.

FIELD OF THE INVENTION

This invention relates to human galactokinase and the identification of galactokinase mutations, a missense and nonsense, as well as isolated nucleic acids encoding same, recombinant host cell transformed with DNA encoding such proteins and to uses of the expressed proteins and nucleic acid sequences in therapeutic and diagnostic applications.

BACKGROUND OF THE INVENTION

There are numerous inherited human metabolic disorders, most of which are recessive. Many have devastating effects that may include a combination of several clinical features, such as severe mental retardation, impairment of the peripheral nervous system, blindness, hearing deficiency and organomegaly. Most of the disorders are rare. However, the majority of such disorders cannot be treated by drugs.

Galactokinase deficiency is one of three known forms of galactosemia. The other forms are galactose-1-phosphate uridyltransferase deficiency and UDP-galactose-4-epimerase deficiency. All three enzymes are involved in galactose metabolism, i.e., the conversion of galactose to glucose in the body. Galactokinase deficiency is inherited as an autosomal recessive trait with a heterozygote frequency estimated to be 0.2% in the general population (see, e.g., Levy et al., *J. Pediatr.*, 92:871–877 (1978)). Patients with homozygous galactokinase deficiency usually become symptomatic in the early infantile period showing galactosemia, galactosuria, increased galactitol levels, cataracts and in a few cases, mental retardation (Segal et al., *J. Pediatr.*, 95:750–752 (1979)). These symptoms usually improve dramatically with the administration of a galactose free diet. Heterozygotes for galactokinase deficiency are prone to presenile cataracts with the onset during 20–50 years of age (Stambolian et al., *Invest. Ophthal. Vis. Sci.*, 27:429–433 (1986)).

Galactokinase activity has been found in a variety of mammalian tissues, including liver, kidney, brain, lens, placenta, erythrocytes and leukocytes. While the protein has been purified from *E. coli*, the purification of the protein from mammalian tissues has proven difficult due to its low cellular concentration. In addition, the molecular basis of galactokinase deficiency is unknown.

This invention provides a human galactokinase gene. The DNAs of this invention, such as the specific sequences disclosed herein, are useful in that they encode the genetic information required for expression of this protein. Additionally, the sequences may be used as probes in order to isolate and identify additional members, of the family, type and/or subtype as well mutations which may form the basis of galactokinase deficiency which may be characterized by site-specific mutations or by atypical expression of the galactokinase gene. The galactokinase gene is also useful as a diagnostic agent to identify mutant galactokinase proteins or as a therapeutic agent via gene therapy.

The first clinical trials of gene therapy began in 1990. Since that time, more than 70 clinical trial protocols have been reviewed and approved by a regulatory authority such as the NIH's Recombinant Advisory Committee (RAC), see, e.g., Anderson, W. F., *Human Gene Therapy*, 5:281–282 (1994). The therapeutic treatment of diseases and disorders by gene therapy involves the transfer and stable insertion of new genetic information into cells. The correction of a genetic defect by re-introduction of the normal allele of a gene has hence demonstrated that this concept is clinically feasible (see, e.g., Rosenberg et al., *New Eng. J. Med.*, 323: 570 (1990)).

These and additional uses for the reagents described herein will become apparent to those of ordinary skill in the art upon reading this specification.

SUMMARY OF THE INVENTION

This invention provides isolated nucleic acid molecules encoding human galactokinase, as well as nucleic acid molecules encoding missense and nonsense mutations, which includes mRNAs, DNAs (e.g., cDNA, genomic DNA, etc.), as well as antisense analogs thereof and diagnostically or therapeutically useful fragments thereof.

This invention also provides recombinant vectors, such as cloning and expression plasmids useful as reagents in the recombinant production of human galactokinase proteins, as well as recombinant prokaryotic and/or eukaryotic host cells comprising a human galactokinase nucleic acid sequence.

This invention also provides a process for preparing human galactokinase proteins which comprises culturing recombinant prokaryotic and/or eukaryotic host cells, containing a human galactokinase nucleic acid sequence, under conditions promoting expression of said protein and subsequent recovery thereof of said protein. Another related aspect of this invention is isolated human galactokinase proteins produced by said method. In yet another aspect, this invention also provides antibodies that are directed to (i.e., bind) human galactokinase proteins.

This invention also provides an isolated human galactokinase proteins having a missense or nonsense mutation and antibodies (monoclonal or polyclonal) that are specifically reactive with said proteins.

This invention also provides nucleic acid probes and PCR primers comprising nucleic acid molecules of sufficient length to specifically hybridize to human galactokinase sequences.

This invention also provides a method to diagnose human galactokinase deficiency which comprises isolating a nucleic acid sample from an individual and assaying the sequence of said nucleic acid sample with the reference gene of the invention and comparing differences between said sample and the nucleic acid of the instant invention, wherein said differences indicate mutations in the human galactokinase gene isolated from an individual. The sample can be assayed by direct sequence comparison (i.e., DNA sequencing), wherein the sample nucleic acid can be compared to the reference galactokinase gene, by hybridization (e.g., mobility shift assays such as heteroduplex gel electrophoresis, SSCP or other techniques such as Northern or Southern blotting which are based upon the length of the nucleic acid sequence) or other known gel electrophoresis methods such as RLFP (for example, by restriction endonuclease digestion of a sample amplified by PCR (for DNA) or PCR-RT (for RNA)). Alternatively, the diagnostic method comprises isolating cells from an individual containing genomic DNA and assaying said sample (e.g., cellular RNA)

by in situ hybridization using the DNA sequence of the invention, or at least one exon, or a fragment containing at least 15, preferably 18, and more preferably 21 contiguous base pairs as a probe. This invention also provides an antisense oligonucleotide having a sequence capable of binding with mRNAs encoding human galactokinase so as to identify mutant galactokinase genes.

This invention also provides yet another method to diagnose human galactokinase deficiency which comprises obtaining a serum or tissue sample; allowing such sample to come in contact with an antibody or antibody fragment which specifically binds to a mutant human galactokinase protein of the invention under conditions such that an antigen-antibody complex is formed between said antibody (or antibody fragment) and said mutant galactokinase protein; and detecting the presence or absence of said complex.

This invention also provides transgenic non-human animals comprising a nucleic acid molecule encoding human galactokinase. Also provided are methods for use of said transgenic animals as models for disease states, mutation and SAR.

This invention also provides a method for treating conditions which are related to insufficient human galactokinase activity which comprises administering to a patient in need thereof a pharmaceutical composition containing the galactokinase protein of the invention which is effective to supplement a patient's endogenous galactokinase and thereby alleviating said condition.

This invention also provides a method for treating conditions which are related to insufficient human galactokinase activity via gene therapy. An additional, or reference, gene comprising the non-mutant galactokinase gene of the instant invention is inserted into a patient's cells either in vivo or ex vivo. The reference gene is expressed in transfected cells and as a result, the protein encoded by the reference gene corrects the defect (i.e., galactokinase deficiency) thus permitting the transfected cells to function normally and alleviating disease conditions (or symptoms).

BRIEF DESCRIPTION OF THE DRAWINGS

FIGS. 2a, 2b, 2c, and 2d are is the genomic DNA sequence (and single letter amino acid abbreviations SEQ. ID NO:33) for human galactokinase [SEQ ID NO: 7]. The bolded DNA sequence corresponds to the exon regions whereas the normal or unbolded type corresponds to the intron regions of human galactokinase.

DETAILED DESCRIPTION OF THE INVENTION

Figure 1:
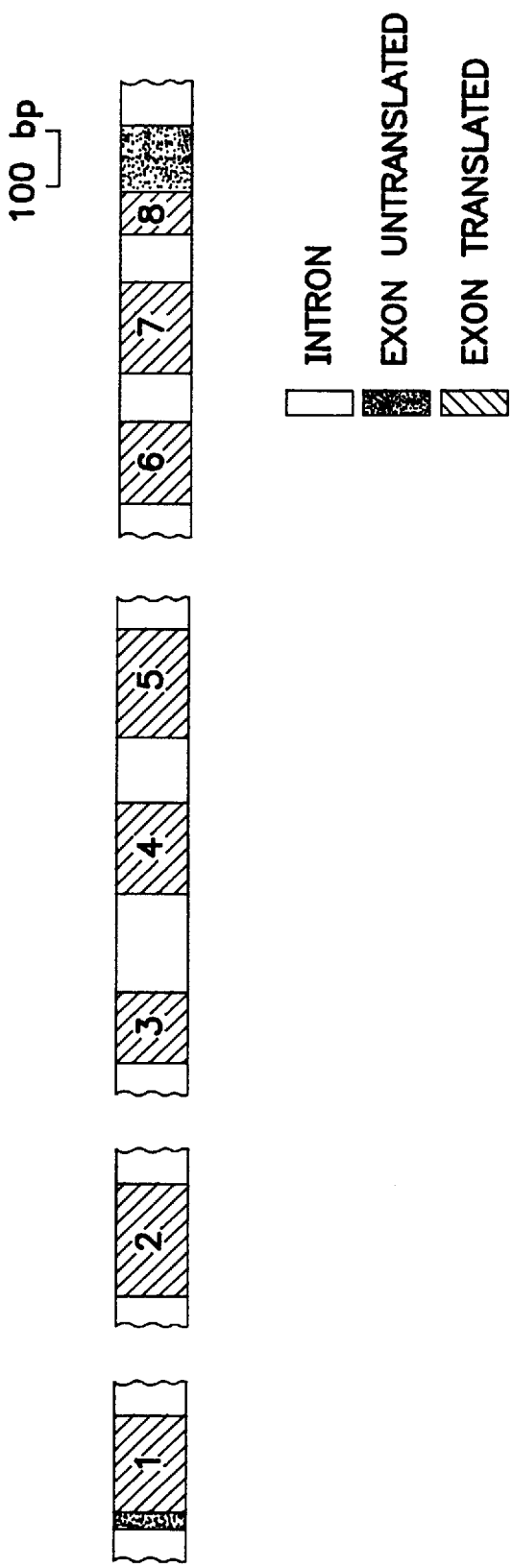
FIG. 1 depicts the intron/exon organization of the human galactokinase gene.

This invention relates to human galactokinase (amino acid and nucleotide sequences) and its use as a diagnostic and therapeutic. The particular cDNA and amino acid sequence of human galactokinase is identified by SEQ ID NO:4 as described more fully below. This invention also relates to the genomic DNA sequence for human galactokinase [SEQ ID NO: 7] and also to mutant human galactokinase genes and amino acid sequences [SEQ ID NOS:5 and 6] and their use for diagnostic purposes.

In further describing the present invention, the following additional terms will be employed, and are intended to be defined as indicated below.

An "antigen" refers to a molecule containing one or more epitopes that will stimulate a host's immune system to make a humoral and/or cellular antigen-specific response. The term is also used herein interchangeably with "immunogen."

The term "epitope" refers to the site on an antigen or hapten to which a specific antibody molecule binds. The term is also used herein interchangeably with "antigenic determinant" or "antigenic determinant site."

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desired protein.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "replication-deficient virus" is a virus in which the excision and/or replication functions have been altered such that after transfection into a host cell, the virus is not able to reproduce and/or infect addition cells.

A "reference" gene refers to the galactokinase sequence of the invention and is understood to include the various sequence polymorphisms that exist, wherein nucleotide substitutions in the gene sequence exist, but do not affect the essential function of the gene product.

A "mutant" gene refers to galactokinase sequences different from the reference gene wherein nucleotide substitutions and/or deletions and/or insertions result in impairment of the essential function of the gene product such that the levels of galactose in an individual (or patient) are atypically elevated. For example, the G to A substitution at position 122 of human galactokinase [SEQ ID NO: 5] is a missense mutation associated with patients who are galactokinase deficient. Another T for G substitution produces an in-frame nonsense codon at amino acid position 80 of the mature protein. The result is a truncated protein consisting of the first 79 amino acids of human galactokinase.

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

"Transfection" or "transfected" refers to a process by which cells take up foreign DNA and integrate that foreign DNA into their chromosome. Transfection can be accomplished, for example, by various techniques in which cells take up DNA (e.g., calcium phosphate precipitation, electroporation, assimilation of liposomes, etc.), or by infection, in which viruses are used to transfer DNA into cells.

A "target cell" is a cell(s) that is selectively transfected over other cell types (or cell lines).

A "clone" is a population of cells derived from a single cell or common ancestor by mitosis. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature. Thus, when the heterologous region encodes a gene, the gene will usually be flanked by DNA that does not flank the gene in the genome of the source animal. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

"Conditions which are related to insufficient human galactokinase activity" or a "deficiency in galactokinase activity" means mutations of the galactokinase protein which affects galactokinase activity or may affect expression of galactokinase or both such that the levels of galactose in a patient are atypically elevated. In addition, this definition is intended to cover atypically low levels of galactokinase expression in a patient due to defective control sequences for the reference galactokinase protein.

This invention provides an isolated nucleic acid molecule encoding a human galactokinase protein and substantially similar sequences. Isolated nucleic acid sequences are "substantially similar" if: (i) they are approximately the same length (i.e., at least 80% of the coding region of SEQ ID NO:4); (ii) they encode a protein with the same (i.e., within an order of magnitude) galactokinase activity as the protein encoded by SEQ ID NO:4; and (iii) they are capable of hybridizing under moderately stringent conditions to SEQ ID NO:4; or they encode DNA sequences which are degenerate to SEQ ID NO:4. Degenerate DNA sequences encode the same amino acid sequence as SEQ ID NO:33, but have variation(s) in the nucleotide coding sequences. Hybridization under moderately stringent conditions is outlined below.

Hybridization under moderately stringent conditions can be performed as follows. Nitrocellulose filters are prehybridized at 65° C. in a solution containing 6× SSPE, 5× Denhardt's solution (10 g Ficoll, 10 g BSA and 10 g Polyvinylpyrrolidone per liter solution), 0.05% SDS and 100 micrograms tRNA. Hybridization probes are labeled, preferably radiolabelled (e.g., using the Bios TAG-IT® kit). Hybridization is then carried out for approximately 18 hours at 65° C. The filters are then washed in a solution of 2× SSC and 0.5% SDS at room temperature for 15 minutes (repeated once). Subsequently, the filters are washed at 58° C., air-dried and exposed to X-ray film overnight at −70° C. with an intensifying screen.

Alternatively, "substantially similar" sequences are substantially the same when about 66% (preferably about 75%, and most preferably about 90%) of the nucleotides or amino acids match over a defined length (i.e., at least 80% of the coding region of SEQ ID NO:4) of the molecule and the protein encoded by such sequence has the same (i.e., within an order of magnitude) galactokinase activity as the protein encoded by SEQ ID NO:4. As used herein, substantially similar refers to the sequences having similar identity to the sequences of the instant invention. Thus nucleotide sequences that are substantially the same can be identified by hybridization or by sequence comparison. Protein sequences that are substantially the same can be identified by one or more of the following: proteolytic digestion, gel electrophoresis and/or microsequencing.

This invention also provides isolated nucleic acid molecules encoding a missense mutation (SEQ ID NO:5) or a nonsense mutation (SEQ ID NO:6) of the human galactokinase protein and DNA sequences which are degenerate to SEQ ID NO: 5 or 6. Degenerate DNA sequences encode the same amino acid (or termination site) sequence as SEQ ID NO: 5 or 6, but have variation(s) in the nucleotide coding sequences.

One means for isolating a nucleic acid molecule encoding for a human galactokinase is to probe a human genomic or cDNA library with a natural or artificially designed probe using art recognized procedures (See for example: "Current Protocols in Molecular Biology", Ausubel, F. M., et al. (eds.) Greene Publishing Assoc. and John Wiley Interscience, New York, 1989, 1992). It is appreciated to one skilled in the art that SEQ ID NO:4, or fragments thereof (comprising at least 15 contiguous nucleotides), is a particularly useful probe. Several particularly useful probes for this purpose are set forth in Table 1, or hybridizable fragments thereof (i.e., comprising at least 15 contiguous nucleotides). It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product.

The probes are thus useful to isolate complementary copies of genomic DNA, cDNA or RNA from human, mammalian or other animal sources or to screen such sources for related sequences (e.g., additional members of the family, type and/or subtype) and including transcriptional regulatory and control elements defined above as well as other stability, processing, translation and tissue specificity-determining regions from 5' and/or 3' regions relative to the coding sequences disclosed herein.

This invention also provides for gene therapy. "Gene therapy" means gene supplementation. That is, an additional (i.e., reference) copy of the gene of interest is inserted into a patients' cells. As a result, the protein encoded by the reference gene corrects the defect (i.e., galactokinase deficiency) and permits the cells to function normally thus alleviating disease symptoms.

Gene therapy of the present invention can occur in vivo or ex vivo. Ex vivo gene therapy requires the isolation and purification of patient cells, the introduction of a therapeutic gene, and introduction of the genetically altered cells back into the patient. A replication-deficient virus such as a modified retrovirus can be used to introduce the therapeutic gene (galactokinase) into such cells. For example, mouse Moloney leukemia virus (MMLV) is a well-known vector in clinical gene therapy trials (see, e.g., Boris-Lauerie et al., *Curr. Opin. Genet. Dev.*, 3:102–109 (1993)).

In contrast, in vivo gene therapy does not require isolation and purification of patients' cells. The therapeutic gene is typically "packaged" for administration to a patient such as in liposomes or in a replication-deficient virus such as adenovirus (see, e.g., Berkner, K. L., *Curr. Top. Microbiol. Immunol.*, 158:39–66 (1992)) or adeno-associated virus (AAV) vectors (see, e.g., Muzyczka, N., *Curr. Top. Microbiol. Immunol.*, 158:97–129 (1992) and U.S. Pat. No. 5,252,479 "Safe Vector for Gene Therapy"). Another approach is administration of so-called "naked DNA" in which the therapeutic gene is directly injected into the bloodstream or muscle tissue.

Cell types useful for gene therapy of the present invention include hepatocytes, fibroblasts, lymphocytes, any cell of the eye (e.g., retina), epithelial and endothelial cells. Preferably the cells are hepatocytes, any cell of the eye or respiratory (or pulmonary) epithelial cells. Transfection of (pulmonary) epithelial cells can occur via inhalation of a neubulized preparation of DNA vectors in liposomes, DNA-protein complexes or replication-deficient adenoviruses (see, e.g., U.S. Pat. No. 5,240,846 "Gene Therapy Vector for Cystic Fibrosis".

This invention also provides for a process to prepare human galactokinase proteins. Non-mutant proteins are defined with reference to the amino acid sequence listed in SEQ ID NO:33 and includes variants with a substantially similar amino acid sequence that have the same galactokinase activity. Additional proteins of this invention include mutant human galactokinase proteins as set forth in SEQ ID NOS: 5 or 6. The proteins of this invention are preferably made by recombinant genetic engineering techniques. The isolated nucleic acids particularly the DNAs can be introduced into expression vectors by operatively linking the DNA to the necessary expression control regions (e.g., regulatory regions) required for gene expression. The vectors can be introduced into the appropriate host cells such as prokaryotic (e.g., bacterial), or eukaryotic (e.g., yeast or mammalian) cells by methods well known in the art (Ausubel et al., supra). The coding sequences for the desired proteins having been prepared or isolated, can be cloned into any suitable vector or replicon. Numerous cloning vectors are known to those of skill in the art, and the selection of an appropriate cloning vector is a matter of choice. Examples of recombinant DNA vectors for cloning and host cells which they can transform include, but is not limited to, the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), a baculovirus insect cell system, a Drosophila insect system, and YCp19 (Saccharomyces). See, generally, "DNA Cloning": Vols. I & II, Glover et al. ed. IRL Press Oxford (1985) (1987) and; T. Maniatis et al. ("Molecular Cloning" Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The subunit antigens of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to produce other mutants or analogs of the galactokinase protein. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of prokaryotic expression vectors are known in the art. See, e.g., U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art See, e.g., U.S. Pat. Nos. 4,446,235; 4,443,539; 4,430,428; see also European Patent Applications 103,409; 100,561; 96,491. pSV2neo (as described in J. Mol. Appl. Genet. 1:327–341) which uses the SV40 late promoter to drive expression in mammalian cells or pCDNA1neo, a vector derived from pCDNA1 (Mol. Cell Biol. 7:4125–29) which uses the CMV promoter to drive expression. Both these latter two vectors can be employed for transient or stable (using G418 resistance) expression in mammalian cells. Insect cell expression systems, e.g., Drosophila, are also useful, see for example, PCT applications WO 90/06358 and WO 92/06212 as well as EP 290,261-B1.

Depending on the expression system and host selected, the proteins of the present invention are produced by growing host cells transformed by an expression vector described above under conditions whereby the protein of interest is expressed. Preferred mammalian cells include human embryonic kidney cells, monkey kidney (HEK-293cells), fibroblast (COS) cells, Chinese hamster ovary (CHO) cells, Drosophila or murine L-cells. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

An alternative method to identify proteins of the present invention is by constructing gene libraries, using the resulting clones to transform E. coli and pooling and screening individual colonies using polyclonal serum or monoclonal antibodies to galactokinase.

The proteins of the present invention may also be produced by chemical synthesis such as solid phase peptide synthesis, using known amino acid sequences or amino acid sequences derived from the DNA sequence of the genes of interest Such methods are known to those skilled in the art. Chemical synthesis of peptides is not particularly preferred.

The proteins of the present invention or their fragments comprising at least one epitope can be used to produce antibodies, both polyclonal and monoclonal. If polyclonal antibodies are desired, a selected mammal, (e.g., mouse, rabbit, goat, horse, etc.) is immunized with the protein of the present invention, or a fragment thereof, capable of eliciting an immune response (i.e., having at least one epitope). Serum from the immunized animal is collected and treated according to known procedures. If serum containing polyclonal antibodies is used, the polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980); see also U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the antigen of interest, or fragment thereof, can be screened for various properties; i.e., for isotype, epitope, affinity, etc. Hence one skilled in the art can produce monoclonal antibodies specifically reactive with mutant galactokinase proteins, e.g., the missense mutation of SEQ ID NO:5 or nonsense mutation of SEQ ID NO:6. Monoclonal antibodies are useful in purification, using immunoaffinity techniques, of the individual antigens which they are directed against. Alternatively, genes encoding the monoclonals of interest may be isolated from the hybridomas by PCR techniques known in the art and cloned and expressed in the appropriate vectors. The antibodies of this invention, whether polyclonal or monoclonal have additional utility in that they may be employed reagents in immunoassays, RIA, ELISA, and the like. As used herein, "monoclonal antibody" is understood to include antibodies derived from one species (e.g., murine, rabbit, goat, rat, human, etc.) as well as antibodies derived from two (or perhaps more) species (e.g., chimeric and humanized antibodies).

Chimeric antibodies, in which non-human variable regions are joined or fused to human constant regions (see, eg. Liu et al., Proc. Natl Acad. Sci, USA, 84:3439 (1987)), may also be used in assays or therapeutically. Preferably, a therapeutic monoclonal antibody would be "humanized" as described in Jones et al., Nature, 321:522 (1986); Verhoeyen et al., Science, 239:1534 (1988); Kabat et al., J. Immunol., 147:1709 (1991); Queen et al., Proc. Natl Acad. Sci. USA, 86:10029 (1989); Gorman et al., Proc. Natl Acad. Sci. USA, 88:34181 (1991); and Hodgson et al., Bio/Technology, 9:421 (1991). Therefore, this invention also contemplates antibodies, polyclonal or monoclonal (including chimeric and "humanized") directed to epitopes corresponding to amino acid sequences disclosed herein from human galactokinase. Methods for the production of polyclonal and monoclonal antibodies are well known, see for example Chap. 11 of Ausubel et al. (supra).

When the antibody is labeled with an analytically detectable reagent such a radioactivity, fluorescence, or an enzyme, the antibody can be use to detect the presence or absence of human galactokinase and/or its quantitative level. In addition, antibodies (polyclonal or monoclonal) specific for the missense and nonsense mutations of the present invention are useful for diagnostic purposes. A serum or tissue sample (e.g., liver, lung, etc.) is obtained and allowed to come in contact with an antibody or antibody fragment which specifically binds to a mutant human galactokinase protein of the invention under conditions such that an antigen-antibody complex is formed between said antibody (or antibody fragment) and said mutant galactokinase protein. The detection for the presence or absence of said complex is within the skill of the art (e.g., ELISA, RIA, Western Blotting, Optical Biosensor (e.g., BIAcore-Pharmacia Biosensor, Uppsala, Sweden) and do not limit this invention.

This invention also contemplates pharmaceutical compositions comprising an effective amount of the galactokinase protein of the invention and a pharmaceutically acceptable carrier. Pharmaceutical compositions of proteinaceous drugs of this invention are particularly useful for parenteral administration, i.e., subcutaneously, intramuscularly or intravenously. Optionally, the galactokinase protein is surrounded by a membrane bound vesicle, such as a liposome.

The compositions for parenteral administration will commonly comprise a solution of the compounds of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well known sterilization techniques. The compositions may contain pharmaceutically acceptable auxiliary substances as required to approximate physiological conditions such as pH adjusting and buffering agents, etc. The concentration of the compound of the invention in such pharmaceutical formulation can very widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg of a compound of the invention. Similarly, a pharmaceutical composition of the invention for intravenous infusion could be made up to contain 250 ml of sterile Ringer's solution, and 150 mg of a compound of the invention. Actual methods for preparing parenterally administrable compositions are well known or will be apparent to those skilled in the art and are described in more detail in, for example, *Remington's Pharmaceutical Science*, 15th ed., Mack Publishing Company, Easton, Pa.

The compounds described herein can be lyophilized for storage and reconstituted in a suitable carrier prior to use. This technique has been shown to be effective with conventional proteins and art-known lyophilization and reconstitution techniques can be employed.

The physician will determine the dosage of the present therapeutic agents which will be most suitable and it will vary with the form of administration and the particular compound chosen, and furthermore, it will vary with the particular patient under patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The therapeutic dosage will generally be from 1 to 10 milligrams per day and higher although it may be administered in several different dosage units.

Depending on the patient condition, the pharmaceutical composition of the invention can be administered for prophylactic and/or therapeutic treatments. In therapeutic application, compositions are administered to a patient already suffering from a disease in an amount sufficient to cure or at least partially arrest the disease and its complications. In prophylactic applications, compositions containing the present compounds or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the compounds of the invention sufficient to effectively treat the patient.

This invention also contemplates use of the galactokinase genes of the instant invention as a diagnostic. For example, some diseases result from inherited defective genes. These genes can be detected by comparing the sequence of the defective gene with that of a normal one. Subsequently, one can verify that a "mutant" gene is associated with galactokinase deficiency by measurement of galactose. That is, a mutant gene would be associated with (atypically) elevated levels of galactose in a patient. In addition, one can insert mutant galactokinase genes into a suitable vector for expression in a functional assay system (e.g., colorimetric assay, expression on MacConkey plates, complementation experiments, e.g, in a galactokinase deficient strain of yeast or *E. coli*) as yet another means to verify or identify galactokinase mutations. As an example, RNA from an individual can be transcribed with reverse transcriptase to cDNA which can then be amplified by polymerase chain reaction (PCR), cloned into an *E. coli* expression vector, and transformed into a galactokinase-deficient strain of *E. coli*. When grown on MacConkey indicator plates, galactokinase-deficient cells will produce colonies that are white in color, whereas cells that have been transformed/complemented with a functional galactokinase gene will be red (see, e.g., Examples section). If most to all of the colonies from an individual are red, then the individual is considered to be normal with respect to galactokinase activity. If approximately 50% of the colonies are red (the other 50% white), then that individual is likely to be a carrier for galactokinase deficiency. If most to all of the colonies are white, then that individual is likely to be galactokinase deficient. Once "mutant" genes have been identified, one can then screen the population for carriers of the "mutant" galactokinase gene. (A carrier is a person in apparent health whose chromosomes contain a "mutant" galactokinase gene that may be transmitted to that person's offspring.) In addition, monoclonal antibodies that are specific for the mutant galactokinase proteins can be used for diagnostic purposes as described above.

Individuals carrying mutations in the human galactokinase gene may be detected at the DNA level by a variety of techniques. Nucleic acids used for diagnosis (genomic DNA, mRNA, etc.) may be obtained from a patient's cells, such as from blood, urine, saliva, tissue biopsy (e.g., chorionic villi sampling or removal of amniotic fluid cells), and autopsy material. The genomic DNA may be used directly for detection or may be amplified enzymatically by using PCR, ligase chain reaction (LCR), strand displacement amplification (SDA), etc. (see, e.g., Saiki et al., *Nature*, 34:163–166 (1986), Bej, et al., *Crit. Rev. Biochem. Molec. Biol.*, 26:301–334 (1991), Birkenmeyer et al., *J. Virol. Meth.*, 35:117–126 (1991), Van Brunt, J., *Bio/Technology*, 8:291–294 (1990)) prior to analysis. RNA may also be used for the same purpose. The RNA can be reverse-transcribed and amplified at one time with PCR-RT (polymerase chain reaction-reverse transcriptase) or reverse-transcribed to an unamplified cDNA. As an example, PCR primers complementary to the nucleic acid of the instant invention can be used to identify and analyze galactokinase mutations. For example, deletions and insertions can be detected by a change in size of the amplified product in comparison to the normal galactokinase genotype. Point mutations can be identified by hybridizing amplified DNA to radiolabeled galactokinase RNA (of the invention) or alternatively, radiolabelled galactokinase antisense DNA sequences (of the invention). Perfectly matched sequences can be distinguished from mismatched duplexes by RNase A digestion or by differences in melting temperatures (Tm). Such a diagnostic would be particularly useful for prenatal and even neonatal testing.

In addition, point mutations and other sequence differences between the reference gene and "mutant" genes can be identified by yet other well-known techniques, e.g., direct DNA sequencing, single-strand conformational polymorphism (SSCP; Orita et al., *Genomics*, 5:874–879 (1989)). For example, a sequencing primer is used with double-stranded PCR product or a single-stranded template molecule generated by a modified PCR. The sequence determination is performed by conventional procedures with radiolabeled nucleotides or by automatic sequencing procedures with fluorescent-tags. Cloned DNA segments may also be used as probes to detect specific DNA segments. The sensitivity of this method is greatly enhanced when combined with PCR. The presence of nucleotide repeats may correlate to a change in galactokinase activity (causative change) or serve as marker for various polymorphisms.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)). In addition, sequence alterations, in particular small deletions, may be detected as changes in the migration pattern of DNA heteroduplexes in non-denaturing gel electrophoresis (i.e., heteroduplex electrophoresis) (see, e.g., Nagamine et al., *Am. J. Hum. Genet.*, 45:337–339 (1989)).

Sequence changes at specific locations may also be revealed by nuclease protection assays, such as RNase and SI protection or the chemical cleavage method (e.g., Cotton et al., *Proc. Natl. Acad. Sci. USA*, 85:4397–4401 (1985)).

Thus, the detection of a specific DNA sequence may be achieved by methods such as hybridization (e.g., heteroduplex electroporation, see, White et al., *Genomics*, 12:301–306 (1992), RNAse protection (e.g., Myers et al., *Science*, 230:1242 (1985)) chemical cleavage (e.g., Cotton et al., *Proc. Natl. Acad. Sci. USA*, 85:4397–4401 (1985))), direct DNA sequencing, or the use of restriction enzymes (e.g., restriction fragment length polymorphisms (RFLP) in which variations in the number and size of restriction fragments can indicate insertions, deletions, presence of nucleotide repeats and any other mutation which creates or destroys an endonuclease restriction sequence). Southern blotting of genomic DNA may also be used to identify large (i.e., greater than 100 base pair) deletions and insertions.

In addition to more conventional gel-electrophoresis, and DNA sequencing, mutations (e.g., microdeletions, aneuploidies, translocations, inversions) can also be detected by in situ analysis (See, e.g., Keller et al., DNA Probes, 2nd Ed., Stockton Press, New York, N.Y., USA (1993)). That is, DNA (or RNA) sequences in cells can be analyzed for mutations without isolation and/or immobilization onto a membrane. Fluorescence in situ hybridization (FISH) is presently the most commonly applied method and numerous reviews of FISH have appeared. See, e.g., Trachuck et al., *Science*, 250:559–562 (1990), and Trask et al., *Trends. Genet.*, 7:149–154 (1991) which are incorporated herein by reference for background purposes. Hence, by using nucleic acids based on the structure of specific genes, e.g., galactokinase, one can develop diagnostic tests for galactokinase deficiency.

In addition, some diseases are a result of, or are characterized by, changes in gene expression which can be detected by changes in the mRNA. Alternatively, the galactokinase gene can be used as a reference to identify individuals expressing a decreased level of galactokinase, e.g., by Northern blotting or in situ hybridization.

Defining appropriate hybridization conditions is within the skill of the art. See, e.g., "Current Protocols in Mol. Biol." Vol. I & II, Wiley Interscience. Ausbel et al. (ed.) (1992). Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. As a general rule the more stringent the hybridization conditions the more closely related genes will be that are recovered.

Also within the scope of this invention are antisense oligonucleotides predicated upon the sequences disclosed herein for human galactokinase. Synthetic oligonucleotides or related antisense chemical structural analogs are designed to recognize and specifically bind to a target nucleic acid encoding galactokinase and galactokinase mutations. The general field of antisense technology is illustrated by the following disclosures which are incorporated herein by reference for purposes of background (Cohen, J. S., *Trends in Pharm. Sci.*, 10:435(1989) and Weintraub, H. M. *Scientific American*, January(1990) at page 40).

Transgenic, non-human, animals may be obtained by transfecting appropriate fertilized eggs or embryos of a host with nucleic acids encoding human galactokinase disclosed herein, see for example U.S. Pat. Nos. 4,736,866; 5,175,385; 5,175,384 and 5,175,386. The resultant transgenic animal may be used as a model for the study of galactokinase. Particularly, useful transgenic animals are those which display a detectable phenotype associated with the expression of the receptor. Drugs may then be screened for their ability to reverse or exacerbate the relevant phenotype. This invention also contemplates operatively linking the receptor coding gene to regulatory elements which are differentially responsive to various temperature or metabolic conditions, thereby effectively turning on or off the phenotypic expression in response to those conditions.

Although not necessarily limiting of this invention, following are some experimental data illustrative of this invention.

EXAMPLE I

Purification of Human Galactokinase from Placental Tissue

Galactokinase (galK) was obtained from human placenta as described by Stambolian et al. (*Biochim Biophys Acta*, 831:306–312 (1985)), which is incorporated by reference in its entirety. In essence, human placenta tissue (obtained within 1 hour of parturition) was homogenized, centrifuged and the resulting supernatant was absorbed onto DEAE-Sephacel®. The material was eluted, precipitated with ammonium sulfate and then run through a sizing column (Sephadex G-100 SF®). Pooled active fractions were concentrated. Purified protein was obtained following separation by SDS polyacrylamide electrophoresis and then Western blotted using standard techniques (see, Laemmli, *Nature*, 227:680–685 (1970), or LeGendre et al., *Biotechniques*, 6:154 (1988)). Minute amounts of galactokinase were isolated (micrograms) from multiple rounds of protein purification. After a trypsin peptide digest, 7 peptide sequences were eventually isolated and identified. The three longest fragments are presented below:

[SEQ ID NO:1]
Val Asn Leu Ile Gly Glu His Thr Asp Tyr Asn Gln Gly Leu Val Leu-Pro Met Ala Leu Glu Leu Met Thr Val Leu Val Gly Ser Pro Arg
[SEQ ID NO:2]
His Ile Gln Glu His Tyr Gly Gly Thr Ala Thr Phe Tyr Leu Ser Gln-Ala Ala Asp Gly Ala Lys
[SEQ ID NO:3]
Ala Gln Val Cys Gln Gln Ala Glu His Ser Phe Ala Gly Met Pro Cys-Gly Ile Met Asp Gln Phe Ile Ser Leu Met Gly Gln Lys

The fragments were compared with peptide sequences encoded by cDNAs, in which the cDNAs were partially sequenced. The cDNAs (also known as expressed sequence tags or ESTs) were obtained from Human Genome Sciences, Inc. (Rockville, Md., USA). The best alignments occurred with an EST sequence from a human osteoclastoma stromal cell library (SEQ ID NO:1 showed 100% identity over 18 contiguous amino acids) and an EST sequence from a human pituitary library (SEQ ID NO:2 showed 95.5% identity over 22 contiguous amino acids). A full-length cDNA from the human osteoclastoma stromal cell library was identified and sequenced (SEQ ID NO:4) in its entirety on an automated ABI 373A Sequencer. Sequencing was confirmed on both strands. The corresponding amino acid sequence (SEQ ID NO:33) was compared against the peptide fragments identified above. SEQ ID NO:1 corresponds to amino acids 38–68 of the full-length human galactokinase protein. Similarly, SEQ ID NOs: 2 and 3 correspond to amino acids 367–388 and 167–195, respectively, of human galactokinase.

Analysis of the Human Galactokinase Gene:

A comparison of the amino acid sequence for human galactokinase with that of *E. coli* galactokinase (Debouck et al., *Nuc. Acid Res.*, 13:1841–1853 (1985)) shows 61% similarity and 44.5% identity. Further comparison with another purported human galactokinase gene (GK2) (Lee et al., *Proc. Natl. Acad. Sci. USA*, 89:10887–10891 (1992)) shows 54% similarity and 34.6% identity at the amino acid level. Furthermore, the GK2 gene maps to human chromosome 15 which is in contrast to the gene of the present invention which maps to human chromosome 17, position q24 as determined by fluorescence in situ hybridization (FISH) analysis.

SEQ ID NO:4 was hybridized against a Northern blot containing human messenger RNA from placenta, brain, skeletal muscle, kidney, intestine, heart, lung and liver according to standard procedures (see, e.g., Sambrook et al., *Molecular Cloning: A Laboratory Manual*, 2nd Ed., Cold Spring Harbor Laboratory Press, 1989). Hybridization was strongest with human liver and lung tissue.

Galactokinase Complementation:

SEQ ID NO:4 was subcloned into an *E. coli* vector, plasmid pBluescript [Stratagene]. When transformed into C600K-, a galactokinase-deficient strain, the transformed *E. coli* grew on MacConkey agar plates containing 1% galactose (and ampicillin @ 50 ug/ml for plasmid selection), and produced brick red colonies, indicating sugar fermentation. Specifically, the red color is due to the action of acids, produced by galactose fermentation, upon bile salts and the indicator (neutral red) in MacConkey medium.

Expression in Mammalian Cells:

SEQ ID NO:4 was also subcloned into COS-1 cells. [ATCC CRL 1650]. The cells were transfected, grown, and cell lysates were prepared. The lysates were assayed by a $^{14}C$ galactokinase assay as described by Stambolian et al. (*Exp. Eye Res.*, 38:231–237 (1984)) which is hereby incorporated by reference in its entirety. When expressed in transiently transfected COS cells, galactokinase activity was tenfold higher than control levels (6600 vs. 640 counts per minute—repeated three times). These results definitively confirm that SEQ ID NO:4 encodes a full-length, biologically active, human galactokinase gene.

The nucleic acid molecule of the invention can also be subcloned into an expression vector to produce high levels of human galactokinase (either fused to another protein, e.g., operatively linked at the 5' end with another coding sequence, or unfused) in transfected cells. For mammalian cells, the expression vector would optionally encode a neomycin resistance gene to select for transfectants on the basis of ability to grow in G418 and a dihydrofolate reductase gene which permits amplification of the transfected gene in DHFR$^-$ cells. The plasmid can then be introduced into host cell lines e.g., CHO ACC98, a nonadherent, DHFR$^-$ cell line adapted to grow in serum free medium, and human embryonic kidney 293 cells (ATCC CRL 1573), and transfected cell lines can be selected by G418 resistance.

Human Galactokinase Gene-Genomic Sequence:

A full-length galactokinase genomic gene coding region was identified from a lambda phage (λ Fix II) human genomic library (made from human placenta tissue) using the galK cDNA as a probe. One isolate, designated clone 17 was deposited on 3 May 1995, with the American Type Culture Collection (ATCC), Rockville, Md., USA, under accession number ATCC 97135, and has been accepted as a patent deposit, in accordance with the Budapest Treaty of 1977 governing the deposit of microorganisms for the purposes of patent procedure.

The genomic gene coding region is divided into at least 8 exons isolated from 4 DNA fragments. The arrangement is depicted in FIG. 1. The DNA sequence was determined by using multiple oligonucleotide PCR primers corresponding to the galK cDNA sequence (i.e., corresponding to galK genomic exons) as well as oligonucleotide PCR primers subsequently designed that correspond to non-coding regions (i.e., galK genomic introns). Thus the structure of the galactokinase genomic gene is summarized in Table 1 below (see also FIG. 2 and SEQ ID NO:7]):

TABLE 1

Genomic Galactokinase Gene

| Exon# | Amino Acids Encoded | PCR Primer #/ [SEQ ID NO] |
|---|---|---|
| 1 | 1–55 | 3333/[8] |
|   |   | 3334/[9] |
|   |   | 3598/[10] |
|   |   | 3599/[11] |
| 2 | 56–118 | 1888/[12] |
|   |   | 3332/[13] |
|   |   | 3604/[14] |
|   |   | 3605/[15] |
| 3 | 119–158 | 3331/[16] |
|   |   | 3606/[17] |
| 4 | 159–204 | 1657/[18] |
|   |   | 3034/[19] |
| 5 | 205–264 | 3330/[20] |
|   |   | 3607/[21] |
| 6 | 265–315 | 1539/[22] |

TABLE 1-continued

Genomic Galactokinase Gene

| Exon# | Amino Acids Encoded | PCR Primer #/ [SEQ ID NO] |
|---|---|---|
| 7 | 316–369 | 2665/[23] 1891/[24] 2665/[25] |
| 8 | 370–392 | 2665/[26] 2666/[27] 2667/[28] |

Galactokinase Deficiency Marker/Gene:

A fibroblast cell line (GM00334), derived from a patient with galactokinase deficiency, was obtained from the Coriell Institute for Medical research, 401 Haddon Ave., Camden, N.J. 08103. Total RNA was isolated from the cultured cells using the RNAZOL kit for isolation of RNA (Biotecx, Houston, Tex.). Cytoplasmic DNA (1 ug) was reversed transcribed with oligonucleotide primers 1823 [SEQ ID NO: 29] and 1825 [SEQ ID NO: 30]. The sample was amplified by 35 cycles at 94° C. for 1 min., 60° C. for 1 min. and 72° C. for 7 min. The DNA product was purified electrophoretically, ligated to the TA cloning vector (Invitrogen) and sequenced. Twelve cDNAs in total were sequenced (representing cloned PCR products of multiple independent PCR reactions). This procedure was also repeated with cultured fibroblasts from normal controls (i.e., persons not exhibiting galactokinase deficiency).

A comparison with normal controls identified a single base substitution of A for G at position 122 of the "normal" human galactokinase gene [SEQ ID NO: 4]. The result is a missense mutation in amino acid 32 from Val to Met [SEQ ID NO: 5]. The G to A base change creates a MscI endonuclease restriction site (i.e., TGG↓CCA) on the mutant allele. This restriction site was then used to rapidly screen for the mutant allele in the parents of the patient with galactokinase deficiency. In essence, the exon encoding galactokinase residues 1 to 5 (i.e., exon 1, see Table 1) was cloned from a genomic lambda phage library and its DNA sequence was determined, including a portion of the flanking intron sequences. Oligonucleotide primers (X2-5OUT [SEQ ID NO: 31] and X2-3OUT [SEQ ID NO: 32]) were designed to hybridize to intron sequences for the amplification of a 346 bp DNA fragment of the genomic DNA. The PCR product was analyzed for the point mutation via RFLP, that is, the presence of a newly created MscI site as detected by electrophoresis of a 1.5% agarose gel. A "normal" allele remains uncut with the enzyme MscI, and thus migrates as a 346 bp fragment on an agarose gel. The PCR product from the patient with galactokinase deficiency (i.e., the G to A base change) is cleaved with MscI, resulting in two fragments of 193 and 153 bp, respectively. The absence of 346 bp fragment indicates that the patient was homozygous for this allele. In contrast, PCR products from the parents of this patient, followed by a MscI digestion, resulted in three fragments (346, 193 and 153 bp) which is consistent with a heterozygous pattern for the G to A base change. That is, the parents were both carriers of the same mutation.

To determine whether the missense mutation resulted in decreased enzymatic activity, a cDNA clone containing the G to A base change was subcloned into COS cells and assayed for galactokinase activity as previously described. COS cells transfected with cDNA encoding the missense mutation had the same level of galactokinase activity as the host COS cells, namely 0.02 units/ug protein. In contrast, COS cells transfected with the non-mutant galactokinase cDNA [SEQ ID NO:4] had a fifty-fold higher activity compared to the host COS cells (i.e., control). This results supports the $Val^{32}$ to $Met^{32}$ substitution as the cause of the decreased enzymatic activity.

Another mutation was discovered in an unrelated patient having cataracts and diagnosed as galactokinase deficient (galactokinase activity was found to be close to zero). Genomic DNA was isolated from lymphoblastoid cell lines and sequenced by automated sequencing on an ABI 373A sequencer. A single base substitution of T for G resulted in an in-frame nonsense codon (i.e., TAG) at amino acid position 80 [SEQ ID NO:6]. This mutation causes premature termination of human galactokinase, resulting in a truncated protein of 79 amino acids that would be expected to be non-functional. (The genomic DNA of the parents of this patient were heterozygous for this mutation, and hence not galactokinase deficient.)

The above description and examples fully disclose the invention including preferred embodiments thereof. Those skilled in the art will recognize, or be able to ascertain using no more than routine experimentation, many equivalents to the specific embodiments herein. Such equivalents are intended to be within the scope of the following claims.

What is claimed is:

1. A method for detecting a mutation in a human galactokinase gene comprising the steps of:
   (a) obtaining a nucleic acid sample from a human individual;
   (b) obtaining a sample nucleic acid sequence from said nucleic acid sample wherein said sample nucleic acid sequence is selected from the group consisting of the sense or antisense DNA sequence of the galactokinase gene, an RNA transcribed from said galactokinase gene, and a mRNA transcribed from said galactokinase gene; and
   (c) identifying sequence differences between said sample nucleic acid sequence and a reference nucleic acid sequence comprising a nucleotide sequence encoding the amino acid sequence as shown in SEQ ID NO:33, wherein a difference in said sample nucleic acid sequence from said reference nucleic acid sequence indicates a mutation in the galactokinase gene of said human individual.

2. The method of claim 1 wherein said sample nucleic acid sequence and said reference nucleic acid sequence are genomic DNA.

3. The method of claim 1 wherein step (c) comprises the steps of reverse transcribing said sample nucleic acid sequence and said reference nucleic acid sequence to obtain a corresponding cDNA sequence for each, and amplifying said corresponding cDNA sequences.

4. The method of claim 1 wherein step (c) comprises digesting said sample nucleic acid sequence and said reference nucleic acid sequence with at least one restriction endonuclease.

5. The method of claim 4 wherein said restriction endonuclease is Msc I.

6. The method of claim 1 wherein step (c) comprises hybridizing said sample nucleic acid sequence to said reference nucleic acid sequence, wherein a mismatched duplex indicates a mutation in said nucleic acid sequence.

7. The method of claim 6 wherein hybridizing comprises comparing mobility of a heteroduplex between said sample nucleic acid sequence and said reference nucleic acid sequence to a homoduplex of said reference nucleic acid sequence.

8. The method of claim 1 wherein step (c) comprises identifying differences in restriction fragment length polymorphisms between said sample nucleic acid sequence and said reference nucleic acid sequence.

9. The method of claim 1 wherein step (c) comprises determining the nucleotide sequence for said sample nucleic acid sequence and said reference nucleic acid sequence.

10. The method of claim 1, wherein said reference nucleic acid sequence comprises the nucleotide sequence as set forth in SEQ ID NO: 4.

11. The method as recited in claim 6 wherein said mismatched duplex is detected using a method selected from the group consisting of RNase digestion and determination of a duplex DNA melting temperature.

12. The method as recited in claim 1 wherein step (c) comprises using gel electrophoresis to detect a sequence difference between said sample nucleic acid sequence and said reference nucleic acid sequence.

13. The method as recited in claim 1 wherein step (c) comprises a method selected from the group consisting of a nuclease protection assay, in situ hybridization analysis, Southern blotting and northern blotting.

14. A method for detecting a mutation in a human galactokinase gene comprising the steps of:
  (a) obtaining a nucleic acid sample from a human individual;
  (b) obtaining a sample nucleic acid sequence from said nucleic acid sample, wherein said sample nucleic acid sequence is selected from the group consisting of the sense or antisense DNA sequence of the galactokinase gene, an RNA transcribed from said galactokinase gene, and a mRNA transcribed from said galactokinase gene;
  (c) identifying a nucleotide sequence-specific property for said sample nucleic acid sequence; and
  (d) comparing said sample nucleic acid sequence and a reference nucleic acid sequence comprising a nucleotide sequence encoding the amino acid sequence as shown in SEQ ID NO:33, with respect to said nucleotide sequence-specific property, wherein a difference with respect to said nucleotide sequence-specific property between said sample nucleic acid sequence and said reference nucleic acid sequence indicates a mutation in the galactokinase gene of said human individual.

15. The method of claim 14 wherein said sample nucleic acid sequence and said reference nucleic acid sequence are genomic DNA.

16. The method of claim 14, wherein said reference nucleic acid sequence comprises the nucleotide sequence as set forth in SEQ ID NO: 4.

17. The method of claim 14 wherein step (c) comprises the steps of reverse transcribing said sample nucleic acid sequence and said reference nucleic acid sequence to obtain a corresponding cDNA sequence for each, and amplifying said corresponding cDNA sequences.

18. The method of claim 14 wherein step (c) comprises digesting said sample nucleic acid sequence and said reference nucleic acid sequence with at least one restriction endonuclease.

19. The method of claim 18 wherein said restriction endonuclease is Msc I.

20. The method of claim 14 wherein step (c) comprises hybridizing said sample nucleic acid sequence to said reference nucleic acid sequence, wherein a mismatched duplex indicates a mutation in said nucleic acid sequence.

21. The method of claim 20 wherein hybridizing comprises comparing mobility of a heteroduplex between said sample nucleic acid sequence and said reference nucleic acid sequence to a homoduplex of said reference nucleic acid sequence.

22. The method of claim 14 wherein step (c) comprises identifying differences in restriction fragment length polymorphisms between said sample nucleic acid sequence and said reference nucleic acid sequence.

23. The method of claim 14 wherein step (c) comprises determining the nucleotide sequence for said sample nucleic acid sequence and said reference nucleic acid sequence.

24. The method as recited in claim 23 wherein step (c) further comprises determining the predicted amino acid sequence encoded by the nucleotide sequence for said sample nucleic acid sequence and step (d) comprises comparing said predicted amino acid sequence to the amino acid set forth in SEQ ID NO: 33.

25. The method as recited in claim 20 wherein said mismatched duplex is detected using a method selected from the group consisting of RNase digestion and determination of a duplex DNA melting temperature.

26. The method as recited in claim 14 wherein step (c) comprises using gel electrophoresis to detect a sequence difference between said sample nucleic acid sequence and said reference nucleic acid sequence.

27. The method as recited in claim 14 wherein step (c) comprises a method selected from the group consisting of a nuclease protection assay, in situ hybridization analysis, Southern blotting and northern blotting.

28. A method for detecting a mutation in a human galactokinase gene comprising the steps of:
  (a) obtaining a nucleic acid sample from a human individual;
  (b) obtaining a sample nucleic acid sequence from said nucleic acid sample, wherein said sample nucleic acid sequence is selected from the group consisting of the sense or antisense DNA sequence of the galactokinase gene, an RNA transcribed from said galactokinase gene, and a mRNA transcribed from said galactokinase gene, and determining the nucleotide sequence of said sample nucleic acid sequence and determining the predicted amino acid sequence encoded thereby; and
  (c) identifying sequence differences between said predicted amino acid sequence and a reference nucleic acid sequence comprising the amino acid sequence as shown in SEQ ID NO:33, wherein a difference in said predicted amino acid sequence from said reference nucleic acid sequence indicates a mutation in the galactokinase gene of said human individual.

29. A method for detecting a mutation in a human galactokinase gene comprising the steps of:
  (a) obtaining a genomic DNA sample from a human individual;
  (b) obtaining a sample genomic DNA sequence corresponding to the galactokinase gene from said genomic DNA sample; and
  (c) identifying sequence differences between said sample genomic DNA sequence and a reference nucleic acid sequence comprising a DNA segment consisting of the nucleotide sequence as set forth in SEQ ID NO:4, a fragment of said DNA sequence comprising at least one galactokinase exon or a fragment of said DNA sequence at least 15 nucleotides in length, wherein a difference in said sample genomic DNA sequence from said reference DNA sequence indicates a mutation in the galactokinase gene of said human individual.

30. A method for detecting a mutation in a human galactokinase gene comprising the steps of:

(a) obtaining a nucleic acid sample from a human individual;

(b) obtaining a sample genomic DNA sequence corresponding to the galactokinase gene from said genomic DNA sample;

(c) identifying a nucleotide sequence-specific property for said sample genomic DNA sequence; and (d) comparing said sample genomic DNA sequence and a reference nucleic acid sequence comprising a DNA segment consisting of the nucleotide sequence as set forth in SEQ ID NO:4, a fragment of said DNA sequence comprising at least one galactokinase exon or a fragment of said DNA sequence at least 15 nucleotides in length, wherein a difference with respect to said nucleotide sequence-specific property between said sample genomic DNA sequence and said reference nucleic acid sequence indicates a mutation in the galactokinase gene of said human individual.

31. A method for detecting a mutation in a human galactokinase gene comprising the steps of:

(a) obtaining a nucleic acid sample from a human individual;

(b) obtaining a sample nucleic acid sequence from said nucleic acid sample, wherein said sample nucleic acid sequence is selected from the group consisting of the sense or antisense DNA sequence of the galactokinase gene, an RNA transcribed from said galactokinase gene, and a mRNA transcribed from said galactokinase gene; and (c) identifying sequence differences between said sample nucleic acid sequence and a reference nucleic acid sequence consisting of a nucleotide sequence selected from the group consisting of the nucleotide sequence as set forth in SEQ ID NO:5 and the nucleotide sequence as set forth in SEQ ID NO:6, wherein no sequence difference between said sample nucleic acid sequence and said reference nucleic acid sequence indicates a mutation in the galactokinase gene of said human individual.

32. A method for detecting a mutation in a human galactokinase gene comprising the steps of:

(a) obtaining a nucleic acid sample from a human individual;

(b) obtaining a sample nucleic acid sequence from said nucleic acid sample, wherein said sample nucleic acid sequence is selected from the group consisting of the sense or antisense DNA sequence of the galactokinase gene, an RNA transcribed from said galactokinase gene, and a mRNA transcribed from said galactokinase gene;

(c) identifying a nucleotide sequence-specific property for said sample nucleic acid sequence; and (d) comparing said sample nucleic acid sequence and a reference nucleic acid sequence consisting of a nucleotide sequence selected from the group consisting of the nucleotide sequence as set forth in SEQ ID NO:5 and the nucleotide sequence as set forth in SEQ ID NO:6, with respect to said nucleotide sequence-specific property, wherein no difference between said sample nucleic acid sequence and said reference nucleic acid sequence indicates a mutation in the galactokinase gene of said human individual.

33. A method for detecting a mutation in a human galactokinase gene comprising:

isolating a nucleic acid sample from an individual;

obtaining, from said nucleic acid sample, a nucleic acid sequence corresponding to a reference galactokinase gene encoding the amino acid sequence as set forth in SEQ ID NO: 33;

inserting said nucleic acid sequence into an expression vector;

introducing said expression vector into a host cell;

culturing said host cell under conditions such that said nucleic acid sequence is expressed; and determining whether an altered level of galactose is produced by said host cell as compared to a host cell which expresses said reference galactokinase gene, wherein an altered level of galactose production indicates a mutation in the galactokinase gene of said individual.

34. A method for detecting a mutation in a human galactokinase gene comprising:

isolating a nucleic acid sample from an individual;

obtaining, from said nucleic acid sample, a nucleic acid sequence corresponding to a reference galactokinase gene encoding the amino acid sequence as set forth in SEQ ID NO: 33;

inserting said nucleic acid sequence into an expression vector;

introducing said expression vector into a host cell;

culturing said host cell under conditions whereby said nucleic acid sequence is expressed; and determining whether enzymatically active human galactokinase is produced.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Val  Asn  Leu  Ile  Gly  Glu  His  Thr  Asp  Tyr  Asn  Gln  Gly  Leu  Val  Leu
 1              5                        10                         15
```

```
            Pro  Met  Ala  Leu  Glu  Leu  Met  Thr  Val  Leu  Val  Gly  Ser  Pro  Arg
                      2 0                     2 5                          3 0
```

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
    His  Ile  Gln  Glu  His  Tyr  Gly  Gly  Thr  Ala  Thr  Phe  Tyr  Leu  Ser  Gln
    1              5                        1 0                         1 5

Ala  Ala  Asp  Gly  Ala  Lys
                  2 0
```

( 2 ) INFORMATION FOR SEQ ID NO:3:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
    Ala  Gln  Val  Cys  Gln  Gln  Ala  Glu  His  Ser  Phe  Ala  Gly  Met  Pro  Cys
    1              5                        1 0                         1 5

Gly  Ile  Met  Asp  Gln  Phe  Ile  Ser  Leu  Met  Gly  Gln  Lys
                  2 0                   2 5
```

( 2 ) INFORMATION FOR SEQ ID NO:4:

( i ) SEQUENCE CHARACTERISTICS:
        ( A ) LENGTH: 1349 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 29..1204

( x i ) SEQUENCE DESCRIPTION: SEQ ID NO:4:

```
GAATTCGGCA  CGAGTGCAGG  CGCGCGTC  ATG  GCT  GCT  TTG  AGA  CAG  CCC  CAG           5 2
                                 Met  Ala  Ala  Leu  Arg  Gln  Pro  Gln
                                  1                    5

GTC  GCG  GAG  CTG  CTG  GCC  GAG  GCC  CGG  CGA  GCC  TTC  CGG  GAG  GAG  TTC   1 0 0
Val  Ala  Glu  Leu  Leu  Ala  Glu  Ala  Arg  Arg  Ala  Phe  Arg  Glu  Glu  Phe
         1 0                    1 5                    2 0

GGG  GCC  GAG  CCC  GAG  CTG  GCC  GTG  TCA  GCG  CCG  GGC  CGC  GTC  AAC  CTC   1 4 8
Gly  Ala  Glu  Pro  Glu  Leu  Ala  Val  Ser  Ala  Pro  Gly  Arg  Val  Asn  Leu
    2 5                    3 0                    3 5                    4 0

ATC  GGG  GAA  CAC  ACG  GAC  TAC  AAC  CAG  GGC  CTG  GTG  CTG  CCT  ATG  GCT   1 9 6
Ile  Gly  Glu  His  Thr  Asp  Tyr  Asn  Gln  Gly  Leu  Val  Leu  Pro  Met  Ala
                   4 5                    5 0                    5 5

CTG  GAG  CTC  ATG  ACG  GTG  CTG  GTG  GGC  AGC  CCC  CGC  AAG  GAT  GGG  CTG   2 4 4
Leu  Glu  Leu  Met  Thr  Val  Leu  Val  Gly  Ser  Pro  Arg  Lys  Asp  Gly  Leu
              6 0                    6 5                    7 0

GTG  TCT  CTC  CTC  ACC  ACC  TCT  GAG  GGT  GCC  GAT  GAG  CCC  CAG  CGG  CTG   2 9 2
```

|   |   |   |   |   |   |   | Val | Ser | Leu | Leu | Thr | Thr | Ser | Glu | Gly | Ala | Asp | Glu | Pro | Gln | Arg | Leu |   |
|---|---|---|---|---|---|---|---|---|---|---|---|---|---|---|---|---|---|---|---|---|---|---|---|
|   |   |   |   |   |   |   |   |   | 75 |   |   |   |   | 80 |   |   |   |   | 85 |   |   |   |   |

```
CAG  TTT  CCA  CTG  CCC  ACA  GCC  CAG  CGC  TCG  CTG  GAG  CCT  GGG  ACT  CCT        340
Gln  Phe  Pro  Leu  Pro  Thr  Ala  Gln  Arg  Ser  Leu  Glu  Pro  Gly  Thr  Pro
     90             95                            100

CGG  TGG  GCC  AAC  TAT  GTC  AAG  GGA  GTG  ATT  CAG  TAC  TAC  CCA  GCT  GCC        388
Arg  Trp  Ala  Asn  Tyr  Val  Lys  Gly  Val  Ile  Gln  Tyr  Tyr  Pro  Ala  Ala
105                 110                           115                       120

CCC  CTC  CCT  GGC  TTC  AGT  GCA  GTG  GTG  GTC  AGC  TCA  GTG  CCC  CTG  GGG        436
Pro  Leu  Pro  Gly  Phe  Ser  Ala  Val  Val  Val  Ser  Ser  Val  Pro  Leu  Gly
                    125                      130                            135

GGT  GGC  CTG  TCC  AGC  TCA  GCA  TCC  TTG  GAA  GTG  GCC  ACG  TAC  ACC  TTC        484
Gly  Gly  Leu  Ser  Ser  Ser  Ala  Ser  Leu  Glu  Val  Ala  Thr  Tyr  Thr  Phe
               140                      145                       150

CTC  CAG  CAG  CTC  TGT  CCA  GAC  TCG  GGC  ACA  ATA  GCT  GCC  CGC  GCC  CAG        532
Leu  Gln  Gln  Leu  Cys  Pro  Asp  Ser  Gly  Thr  Ile  Ala  Ala  Arg  Ala  Gln
          155                      160                       165

GTG  TGT  CAG  CAG  GCC  GAG  CAC  AGC  TTC  GCA  GGG  ATG  CCC  TGT  GGC  ATC        580
Val  Cys  Gln  Gln  Ala  Glu  His  Ser  Phe  Ala  Gly  Met  Pro  Cys  Gly  Ile
     170                      175                       180

ATG  GAC  CAG  TTC  ATC  TCA  CTT  ATG  GGA  CAG  AAA  GGC  CAC  GCG  CTG  CTC        628
Met  Asp  Gln  Phe  Ile  Ser  Leu  Met  Gly  Gln  Lys  Gly  His  Ala  Leu  Leu
185                      190                      195                      200

ATT  GAC  TGC  AGG  TCC  TTG  GAG  ACC  AGC  CTG  GTG  CCA  CTC  TCG  GAC  CCC        676
Ile  Asp  Cys  Arg  Ser  Leu  Glu  Thr  Ser  Leu  Val  Pro  Leu  Ser  Asp  Pro
                    205                      210                           215

AAG  CTG  GCC  GTG  CTC  ATC  ACC  AAC  TCT  AAT  GTC  CGC  CAC  TCC  CTG  GCC        724
Lys  Leu  Ala  Val  Leu  Ile  Thr  Asn  Ser  Asn  Val  Arg  His  Ser  Leu  Ala
               220                      225                       230

TCC  AGC  GAG  TAC  CCT  GTG  CGG  CGG  CGC  CAA  TGT  GAA  GAA  GTG  GCC  CGG        772
Ser  Ser  Glu  Tyr  Pro  Val  Arg  Arg  Arg  Gln  Cys  Glu  Glu  Val  Ala  Arg
          235                      240                       245

GCG  CTG  GGC  AAG  GAA  AGC  CTC  CGG  GAG  GTA  CAA  CTG  GAA  GAG  CTA  GAG        820
Ala  Leu  Gly  Lys  Glu  Ser  Leu  Arg  Glu  Val  Gln  Leu  Glu  Glu  Leu  Glu
     250                      255                       260

GCT  GCC  AGG  GAC  CTG  GTG  AGC  AAA  GAG  GGC  TTC  CGG  CGG  GCC  CGG  CAC        868
Ala  Ala  Arg  Asp  Leu  Val  Ser  Lys  Glu  Gly  Phe  Arg  Arg  Ala  Arg  His
265                      270                      275                      280

GTG  GTG  GGG  GAG  ATT  CGG  CGC  ACG  GCC  CAG  GCA  GCG  GCC  GCC  CTG  AGA        916
Val  Val  Gly  Glu  Ile  Arg  Arg  Thr  Ala  Gln  Ala  Ala  Ala  Ala  Leu  Arg
                    285                      290                           295

CGT  GGC  GAC  TAC  AGA  GCC  TTT  GGC  CGC  CTC  ATG  GTG  GAG  AGC  CAC  CGC        964
Arg  Gly  Asp  Tyr  Arg  Ala  Phe  Gly  Arg  Leu  Met  Val  Glu  Ser  His  Arg
               300                      305                       310

TCA  CTC  AGA  GAC  GAC  TAT  GAG  GTG  AGC  TGC  CCA  GAG  CTG  GAC  CAG  CTG       1012
Ser  Leu  Arg  Asp  Asp  Tyr  Glu  Val  Ser  Cys  Pro  Glu  Leu  Asp  Gln  Leu
          315                      320                       325

GTG  GAG  GCT  GCG  CTT  GCT  GTG  CCT  GGG  GTT  TAT  GGC  AGC  CGC  ATG  ACG       1060
Val  Glu  Ala  Ala  Leu  Ala  Val  Pro  Gly  Val  Tyr  Gly  Ser  Arg  Met  Thr
     330                      335                       340

GGC  GGT  GGC  TTC  GGT  GGC  TGC  ACG  GTG  ACA  CTG  CTG  GAG  GCC  TCC  GCT       1108
Gly  Gly  Gly  Phe  Gly  Gly  Cys  Thr  Val  Thr  Leu  Leu  Glu  Ala  Ser  Ala
345                      350                      355                      360

GCT  CCC  CAC  GCC  ATG  CGG  CAC  ATC  CAG  GAG  CAC  TAC  GGC  GGG  ACT  GCC       1156
Ala  Pro  His  Ala  Met  Arg  His  Ile  Gln  Glu  His  Tyr  Gly  Gly  Thr  Ala
                    365                      370                           375

ACC  TTC  TAC  CTC  TCT  CAA  GCA  GCC  GAT  GGA  GCC  AAG  GTG  CTG  TGC  TTG       1204
Thr  Phe  Tyr  Leu  Ser  Gln  Ala  Ala  Asp  Gly  Ala  Lys  Val  Leu  Cys  Leu
               380                      385                       390

TGAGGCACCC  CCAGGACAGC  ACACGGTGAG  GGTGCGGGGC  CTGCAGGCCA  GTCCCACGGC              1264
```

```
TCTGTGCCCG GTGCCATCTT CCATATCCGG GTGCTCAATA AACTTGTGCC TCCAATGTGG    1324

AAAAAAAAAA AAAAAAAAAC TCGAG                                         1349
```

( 2 ) INFORMATION FOR SEQ ID NO:5:

( i ) SEQUENCE CHARACTERISTICS:
        ( A ) LENGTH: 1349 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 29..1204

( x i ) SEQUENCE DESCRIPTION: SEQ ID NO:5:

```
GAATTCGGCA CGAGTGCAGG CGCGCGTC ATG GCT GCT TTG AGA CAG CCC CAG       52
                                Met Ala Ala Leu Arg Gln Pro Gln
                                 1                   5

GTC GCG GAG CTG CTG GCC GAG GCC CGG CGA GCC TTC CGG GAG GAG TTC     100
Val Ala Glu Leu Leu Ala Glu Ala Arg Arg Ala Phe Arg Glu Glu Phe
     10              15                  20

GGG GCC GAG CCC GAG CTG GCC ATG TCA GCG CCG GGC CGC GTC AAC CTC     148
Gly Ala Glu Pro Glu Leu Ala Met Ser Ala Pro Gly Arg Val Asn Leu
 25              30                  35                      40

ATC GGG GAA CAC ACG GAC TAC AAC CAG GGC CTG GTG CTG CCT ATG GCT     196
Ile Gly Glu His Thr Asp Tyr Asn Gln Gly Leu Val Leu Pro Met Ala
                 45                  50                  55

CTG GAG CTC ATG ACG GTG CTG GTG GGC AGC CCC CGC AAG GAT GGG CTG     244
Leu Glu Leu Met Thr Val Leu Val Gly Ser Pro Arg Lys Asp Gly Leu
             60                  65                  70

GTG TCT CTC CTC ACC ACC TCT GAG GGT GCC GAT GAG CCC CAG CGG CTG     292
Val Ser Leu Leu Thr Thr Ser Glu Gly Ala Asp Glu Pro Gln Arg Leu
         75                  80                  85

CAG TTT CCA CTG CCC ACA GCC CAG CGC TCG CTG GAG CCT GGG ACT CCT     340
Gln Phe Pro Leu Pro Thr Ala Gln Arg Ser Leu Glu Pro Gly Thr Pro
     90                  95                 100

CGG TGG GCC AAC TAT GTC AAG GGA GTG ATT CAG TAC TAC CCA GCT GCC     388
Arg Trp Ala Asn Tyr Val Lys Gly Val Ile Gln Tyr Tyr Pro Ala Ala
105             110                 115                     120

CCC CTC CCT GGC TTC AGT GCA GTG GTG GTC AGC TCA GTG CCC CTG GGG     436
Pro Leu Pro Gly Phe Ser Ala Val Val Val Ser Ser Val Pro Leu Gly
                125                 130                 135

GGT GGC CTG TCC AGC TCA GCA TCC TTG GAA GTG GCC ACG TAC ACC TTC     484
Gly Gly Leu Ser Ser Ser Ala Ser Leu Glu Val Ala Thr Tyr Thr Phe
            140                 145                 150

CTC CAG CAG CTC TGT CCA GAC TCG GGC ACA ATA GCT GCC CGC GCC CAG     532
Leu Gln Gln Leu Cys Pro Asp Ser Gly Thr Ile Ala Ala Arg Ala Gln
        155                 160                 165

GTG TGT CAG CAG GCC GAG CAC AGC TTC GCA GGG ATG CCC TGT GGC ATC     580
Val Cys Gln Gln Ala Glu His Ser Phe Ala Gly Met Pro Cys Gly Ile
    170                 175                 180

ATG GAC CAG TTC ATC TCA CTT ATG GGA CAG AAA GGC CAC GCG CTG CTC     628
Met Asp Gln Phe Ile Ser Leu Met Gly Gln Lys Gly His Ala Leu Leu
185                 190                 195                 200

ATT GAC TGC AGG TCC TTG GAG ACC AGC CTG GTG CCA CTC TCG GAC CCC     676
Ile Asp Cys Arg Ser Leu Glu Thr Ser Leu Val Pro Leu Ser Asp Pro
                205                 210                 215

AAG CTG GCC GTG CTC ATC ACC AAC TCT AAT GTC CGC CAC TCC CTG GCC     724
Lys Leu Ala Val Leu Ile Thr Asn Ser Asn Val Arg His Ser Leu Ala
```

|  |  |  |  |  | 220 |  |  |  |  | 225 |  |  |  |  | 230 |  |  |
|---|---|---|---|---|---|---|---|---|---|---|---|---|---|---|---|---|---|

```
TCC  AGC  GAG  TAC  CCT  GTG  CGG  CGG  CGC  CAA  TGT  GAA  GAA  GTG  GCC  CGG        772
Ser  Ser  Glu  Tyr  Pro  Val  Arg  Arg  Arg  Gln  Cys  Glu  Glu  Val  Ala  Arg
     235                 240                 245

GCG  CTG  GGC  AAG  GAA  AGC  CTC  CGG  GAG  GTA  CAA  CTG  GAA  GAG  CTA  GAG        820
Ala  Leu  Gly  Lys  Glu  Ser  Leu  Arg  Glu  Val  Gln  Leu  Glu  Glu  Leu  Glu
     250                 255                 260

GCT  GCC  AGG  GAC  CTG  GTG  AGC  AAA  GAG  GGC  TTC  CGG  CGG  GCC  CGG  CAC        868
Ala  Ala  Arg  Asp  Leu  Val  Ser  Lys  Glu  Gly  Phe  Arg  Arg  Ala  Arg  His
265                      270                 275                           280

GTG  GTG  GGG  GAG  ATT  CGG  CGC  ACG  GCC  CAG  GCA  GCG  GCC  GCC  CTG  AGA        916
Val  Val  Gly  Glu  Ile  Arg  Arg  Thr  Ala  Gln  Ala  Ala  Ala  Ala  Leu  Arg
                    285                      290                           295

CGT  GGC  GAC  TAC  AGA  GCC  TTT  GGC  CGC  CTC  ATG  GTG  GAG  AGC  CAC  CGC        964
Arg  Gly  Asp  Tyr  Arg  Ala  Phe  Gly  Arg  Leu  Met  Val  Glu  Ser  His  Arg
               300                      305                 310

TCA  CTC  AGA  GAC  GAC  TAT  GAG  GTG  AGC  TGC  CCA  GAG  CTG  GAC  CAG  CTG       1012
Ser  Leu  Arg  Asp  Asp  Tyr  Glu  Val  Ser  Cys  Pro  Glu  Leu  Asp  Gln  Leu
          315                      320                      325

GTG  GAG  GCT  GCG  CTT  GCT  GTG  CCT  GGG  GTT  TAT  GGC  AGC  CGC  ATG  ACG       1060
Val  Glu  Ala  Ala  Leu  Ala  Val  Pro  Gly  Val  Tyr  Gly  Ser  Arg  Met  Thr
     330                      335                      340

GGC  GGT  GGC  TTC  GGT  GGC  TGC  ACG  GTG  ACA  CTG  CTG  GAG  GCC  TCC  GCT       1108
Gly  Gly  Gly  Phe  Gly  Gly  Cys  Thr  Val  Thr  Leu  Leu  Glu  Ala  Ser  Ala
345                      350                      355                      360

GCT  CCC  CAC  GCC  ATG  CGG  CAC  ATC  CAG  GAG  CAC  TAC  GGC  GGG  ACT  GCC       1156
Ala  Pro  His  Ala  Met  Arg  His  Ile  Gln  Glu  His  Tyr  Gly  Gly  Thr  Ala
                    365                      370                      375

ACC  TTC  TAC  CTC  TCT  CAA  GCA  GCC  GAT  GGA  GCC  AAG  GTG  CTG  TGC  TTG       1204
Thr  Phe  Tyr  Leu  Ser  Gln  Ala  Ala  Asp  Gly  Ala  Lys  Val  Leu  Cys  Leu
               380                      385                      390

TGAGGCACCC  CCAGGACAGC  ACACGGTGAG  GGTGCGGGGC  CTGCAGGCCA  GTCCCACGGC             1264

TCTGTGCCCG  GTGCCATCTT  CCATATCCGG  GTGCTCAATA  AACTTGTGCC  TCCAATGTGG             1324

AAAAAAAAAA  AAAAAAAAAC  TCGAG                                                      1349
```

( 2 ) INFORMATION FOR SEQ ID NO:6:

( i ) SEQUENCE CHARACTERISTICS:
        ( A ) LENGTH: 1349 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 29..265

( x i ) SEQUENCE DESCRIPTION: SEQ ID NO:6:

```
GAATTCGGCA  CGAGTGCAGG  CGCGCGTC  ATG  GCT  GCT  TTG  AGA  CAG  CCC  CAG           52
                                 Met  Ala  Ala  Leu  Arg  Gln  Pro  Gln
                                  1                  5

GTC  GCG  GAG  CTG  CTG  GCC  GAG  GCC  CGG  CGA  GCC  TTC  CGG  GAG  GAG  TTC      100
Val  Ala  Glu  Leu  Leu  Ala  Glu  Ala  Arg  Arg  Ala  Phe  Arg  Glu  Glu  Phe
          10                      15                      20

GGG  GCC  GAG  CCC  GAG  CTG  GCC  GTG  TCA  GCG  CCG  GGC  CGC  GTC  AAC  CTC      148
Gly  Ala  Glu  Pro  Glu  Leu  Ala  Val  Ser  Ala  Pro  Gly  Arg  Val  Asn  Leu
25                       30                      35                           40

ATC  GGG  GAA  CAC  ACG  GAC  TAC  AAC  CAG  GGC  CTG  GTG  CTG  CCT  ATG  GCT      196
Ile  Gly  Glu  His  Thr  Asp  Tyr  Asn  Gln  Gly  Leu  Val  Leu  Pro  Met  Ala
                    45                      50                           55
```

| | | | | | | | | | | | | | | | |
|---|---|---|---|---|---|---|---|---|---|---|---|---|---|---|---|
|CTG|GAG|CTC|ATG|ACG|GTG|CTG|GTG|GGC|AGC|CCC|CGC|AAG|GAT|GGG|CTG|244
|Leu|Glu|Leu|Met|Thr|Val|Leu|Val|Gly|Ser|Pro|Arg|Lys|Asp|Gly|Leu|
| | | |60| | | |65| | | |70| | | | |

| | | | | | | | |
|---|---|---|---|---|---|---|---|
|GTG|TCT|CTC|CTC|ACC|ACC|TCT|TAGGGTGCCG ATGAGCCCCA GCGGCTGCAG|295
|Val|Ser|Leu|Leu|Thr|Thr|Ser| |
| | |75| | | | | |

| | | | | |
|---|---|---|---|---|
|TTTCCACTGC|CCACAGCCCA|GCGCTCGCTG|GAGCCTGGGA|CTCCTCGGTG GGCCAACTAT|355
|GTCAAGGGAG|TGATTCAGTA|CTACCCAGCT|GCCCCCTCC|CTGGCTTCAG TGCAGTGGTG|415
|GTCAGCTCAG|TGCCCCTGGG|GGGTGGCCTG|TCCAGCTCAG|CATCCTTGGA AGTGGCCACG|475
|TACACCTTCC|TCCAGCAGCT|CTGTCCAGAC|TCGGGCACAA|TAGCTGCCCG CGCCCAGGTG|535
|TGTCAGCAGG|CCGAGCACAG|CTTCGCAGGG|ATGCCCTGTG|GCATCATGGA CCAGTTCATC|595
|TCACTTATGG|GACAGAAAGG|CCACGCGCTG|CTCATTGACT|GCAGGTCCTT GGAGACCAGC|655
|CTGGTGCCAC|TCTCGGACCC|CAAGCTGGCC|GTGCTCATCA|CCAACTCTAA TGTCCGCCAC|715
|TCCCTGGCCT|CCAGCGAGTA|CCCTGTGCGG|CGGCGCCAAT|GTGAAGAAGT GGCCCGGGCG|775
|CTGGGCAAGG|AAAGCCTCCG|GGAGGTACAA|CTGGAAGAGC|TAGAGGCTGC CAGGGACCTG|835
|GTGAGCAAAG|AGGGCTTCCG|GCGGGCCCGG|CACGTGGTGG|GGGAGATTCG GCGCACGGCC|895
|CAGGCAGCGG|CCGCCCTGAG|ACGTGGCGAC|TACAGAGCCT|TTGGCCGCCT CATGGTGGAG|955
|AGCCACCGCT|CACTCAGAGA|CGACTATGAG|GTGAGCTGCC|CAGAGCTGGA CCAGCTGGTG|1015
|GAGGCTGCGC|TTGCTGTGCC|TGGGGTTTAT|GGCAGCCGCA|TGACGGGCGG TGGCTTCGGT|1075
|GGCTGCACGG|TGACACTGCT|GGAGGCCTCC|GCTGCTCCCC|ACGCCATGCG GCACATCCAG|1135
|GAGCACTACG|GCGGGACTGC|CACCTTCTAC|CTCTCTCAAG|CAGCCGATGG AGCCAAGGTG|1195
|CTGTGCTTGT|GAGGCACCCC|CAGGACAGCA|CACGGTGAGG|GTGCGGGGCC TGCAGGCCAG|1255
|TCCCACGGCT|CTGTGCCCGG|TGCCATCTTC|CATATCCGGG|TGCTCAATAA ACTTGTGCCT|1315
|CCAATGTGGA|AAAAAAAAA|AAAAAAACT|CGAG| |1349

( 2 ) INFORMATION FOR SEQ ID NO:7:

( i ) SEQUENCE CHARACTERISTICS:
        ( A ) LENGTH: 7676 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

| | | | | |
|---|---|---|---|---|
|CCGAGCATCC|CGCGCCGACG|GGTCTGTGCC|GGAGCAGCTG|TGCAGAGCTG CAGGCGCGCG|60
|TCATGGCTGC|TTTGAGACAG|CCCCAGGTCG|CGGAGCTGCT|GGCCGAGGCC CGGCGAGCCT|120
|TCCGGGAGGA|GTTCGGGGCC|GAGCCCGAGC|TGGCCGTGTC|AGCGCCGGGC CGCGTCAACC|180
|TCATCGGGGA|ACACACGGAC|TACAACCAGG|GCCTGGTGCT|GCCTATGGTG AGGGGCTGCA|240
|CGGGGAGCCC|CTAGCCCGCC|GCCGCCTGTC|CCGGTCGCCG|AGGAGGCGG GCCTCGGGGA|300
|CGCTGGGGGC|GAGTTCTTCC|CGCGGGAGAT|GTGGGCGGG|CAGCTGCGCC TGGAGCACCG|360
|GTGCACGGAA|GAGTCCCCGG|GACAGGCTGT|TCCCCACGTT|GGAAGGGAGG AAGCGAAGAA|420
|GTGGTCCCCA|GAGGGTGCGC|GGCCGCCTCT|TGGCTCAAGC|CCGCCCTCTG GGGGCTGGGG|480
|CTCCTCGCCT|TCAACCTGGG|AGCATGTTCC|CCTTAAACTG|TGAGGCCCTG TGTGCCACGC|540
|AGAAGGGGAC|ACTCCGCGCC|TCCGGCCACC|GTGGGCCCC|AACCGCAGAC CTGGGCGAAC|600
|GTAGCCTTCT|GGCCCAGCCC|GTTCAATTTA|CAGAGGAGGA|AACTGAGGCC TAGAGAGGCC|660

| | | | | | | |
|---|---|---|---|---|---|---|
| CAGTGAACTG | CTGGAGGTCA | CACAGCAGGT | TCTTGGCGGG | GCTGCGACTT | GGGAGTGAGG | 720 |
| ACTCCCAGCT | TTCAGCGGGG | GGCGCTTTCC | GCCCCATCTG | CAGCTTGGGG | AGTGCACAGG | 780 |
| TACAGGATGT | CCAGAGCCAC | CCAAAATGTA | AAGGCTTTGG | AGCTCCAGTG | ATCTGTTTTC | 840 |
| CCTTTGGGCT | AAGCTCTCCC | CCCTTGCCCC | ACAGCTCAGG | GCAGAGTCCA | GGTCTGTGCT | 900 |
| CCAGCTGCAG | CCGCCCCGCC | CCTGAAGACC | TAAGGGGGCA | GGGCTCAAGC | CCCCAAGGTC | 960 |
| AGCTGGCCCT | CAGGATCTTC | CCTGCGACGC | TGAACCTGGA | GGTTCAGAAC | CTGATGACTG | 1020 |
| TGGAGGCATC | AGAACCTCGG | CTGGAGGCAG | TGTCATTGGA | GAGGCTTACT | CCAGCTGGCG | 1080 |
| GAAGCCTCAC | GTACTGCTTG | TCTCTCCTGC | CAGGCTCTGG | AGCTCATGAC | GGTGCTGGTG | 1140 |
| GGCAGCCCCC | GCAAGGATGG | GCTGGTGTCT | CTCCTCACCA | CCTCTGAGGG | TGCCGATGAG | 1200 |
| CCCCAGCGGC | TGCAGTTTCC | ACTGCCCACA | GCCAGCGCT | CGCTGGAGCC | TGGGACTCCT | 1260 |
| CGGTGGGCCA | ACTATGTCAA | GGGAGTGATT | CAGTACTACC | CAGGTATGGG | GCCCAGGCCT | 1320 |
| GAGCCAAGTC | CTCACTGATA | CTAGGAGTGC | CACCTCACAG | CCACAGAGCC | CATTCATTTG | 1380 |
| TCTGATACAC | TGTGGGGAAG | GCTTGTAGAG | TGGAGCATCC | CATTGTACAG | ATGAGGAAAC | 1440 |
| TGATGCCCCC | AGAAGGTCGG | GAACTTGCCC | TGGGTTTCCC | GTGACCTGAT | TGGAGGAGCC | 1500 |
| AGGATTTGAA | CCCCAGCCTT | TTTTCCCTCC | AGAGCCCTAA | ACCAGGAGGA | CAATTAGAAG | 1560 |
| TGTCCCAGCA | ACCTCAGAGG | GTGGGAAAAT | GGAGGGGAGT | GGGTCCCTTG | GGCCAGCAGG | 1620 |
| TTGGTGGGGT | TCTTGACAAT | TGAGACACAC | ACCTAGAAAC | AGTTGCTAGG | CCGTTGCTGC | 1680 |
| CCTTCCCGCC | AGGACACCTG | CCCTTCCTGT | CCAATCCTCC | CAGGCAGCCT | CTCTTACCAT | 1740 |
| CACCTGTTCT | TTCCCCCTGC | AGCTGCCCCC | CTCCCTGGCT | TCAGTGCAGT | GGTGGTCAGC | 1800 |
| TCAGTGCCCC | TGGGGGGTGG | CCTGTCCAGC | TCAGCATCCT | TGGAAGTGGC | CACGTACACC | 1860 |
| TTCCTCCAGC | AGCTCTGTCC | AGGTACCAGC | TAGGCCCCAG | CCCTGACCCA | GCCCTCCTTC | 1920 |
| CCTGAGGTCT | CCAGGTGGTC | CCAGCTTCTA | CTATGCCTTA | TGGAGGGGT | GGCAGGGAAT | 1980 |
| CTCCCTGGAG | TGTCATTGAA | GCCACTGCTG | CTTCCACCAG | CCCTAGCCTC | CCCACCTCAC | 2040 |
| CCTGTACTGC | AGACTCGGGC | ACAATAGCTG | CCCGCGCCCA | GGTGTGTCAG | CAGGCCGAGC | 2100 |
| ACAGCTTCGC | AGGGATGCCC | TGTGGCATCA | TGGACCAGTT | CATCTCACTT | ATGGGACAGA | 2160 |
| AAGGCCACGC | GCTGCTCATT | GACTGCAGGT | TGGGCTCGCT | CCCCTCGTCC | CCTCCCGCCC | 2220 |
| TGCACTCAGC | AGCTCCTGGG | TGGAGTGTGC | CCACTGCCTG | GCGCAGCAAG | CACACGCTTG | 2280 |
| GCCTCGTCAT | CTCCCCCATT | GTAACTCCAC | CCCAGGTCCT | TGGAGACCAG | CCTGGTGCCA | 2340 |
| CTCTCGGACC | CCAAGCTGGC | CGTGCTCATC | ACCAACTCTA | ATGTCCGCCA | CTCCCTGGCC | 2400 |
| TCCAGCGAGT | ACCCTGTGCG | GCGGCGCCAA | TGTGAAGAAG | TGGCCCGGGC | GCTGGGCAAG | 2460 |
| GAAAGCCTCC | GGGAGGTACA | ACTGGAAGAG | CTAGAGGGTG | AGAACTGCCA | GGGTGCTCTA | 2520 |
| TCCTGGAGGC | GGCTGTGCTC | CCTGCTGGCG | CCTCAGTGTG | GCCTTGACCC | TGCCTGGGAC | 2580 |
| CCCGATCTCC | AGGGGCTTCT | GCCATGCTCT | CCCCAGTCCC | TTCAAACACT | GCGCACCCAG | 2640 |
| GGTTCCAATC | TCAGCAGGGG | TGCTTGAAAT | CCTAAAATGG | TCTTATCTAA | TCAGAAAAAT | 2700 |
| CATGTTTCCA | TTGTGGAAAA | TGTAGAAAAG | TACAAAGTAG | AAAATAATAA | GCTATAAGGG | 2760 |
| CACTACCCAG | AGATAGGCAC | TGCTGACATT | TTCACGTTTC | CTTTCAGTAT | TTTTCCACAT | 2820 |
| CTGTCTTCAA | AGCTGAGTAT | ATGTAATATA | TCATCACTTT | CCCCCCCCAC | CCCCTTTTTT | 2880 |
| TTAAGAGGCA | GGGTCTCATT | CTGTTGCCCA | AGCTGGAGTG | TAGTGGTGTG | ATCATAGCTT | 2940 |
| ACTGCAAACT | TGAACTCTTG | AGCTCAAGGG | ATCCTCCCAG | CTCAGCCTTC | CAAGTAGCTG | 3000 |
| AGATTACAGG | TGTGCCACCA | TGCCCGGCTA | ATTTTTATCT | TCGTAAAGAC | GGCCTTGTAG | 3060 |

| | | | | | | |
|---|---|---|---|---|---|---|
| TGTTGCCCAG | GATGATCCTG | AACTCTGGCC | TCAAGAGGTC | CTCCTGCCTT | GGGCTCCCAA | 3120 |
| AGTGTTGGGA | TTATAGGCAT | GAGCCACTGC | GGCCAGCCCA | TTTGCCGTGT | TTTTTTTTG | 3180 |
| GACACAGAGT | TTCGGTCTTG | TCACCCATGC | TGGAGTGCAA | TGGTGCGATC | TCAGCTCACT | 3240 |
| GTAACCTCTG | CCTCCCGGGT | TCAAGTGATT | CTCCTGCCTC | AGCCTCCCGA | GTAGCTGGGA | 3300 |
| CTACAGGCGC | CCGCCACTAC | GCCTGGCACA | TTTTTATAG | TTCTAGTAGA | GACTGGGGTT | 3360 |
| TCACCATGTT | GGCCAGGCTG | GTCTCAAACG | CCTGACCTCA | GGTGATCCTC | CCGCCTCAGC | 3420 |
| CTTCCAAAGT | GCTGGGATTA | CAGGCGTGAG | CCATAGTGCC | GGTCTCTTTT | TTTTTTTTT | 3480 |
| TTAAACTAAA | CATAATCTCA | GAACCCAGAA | CCCTATCTTA | TCTTATGCCA | TGAAAGGCAT | 3540 |
| ATCTCGGCGT | GGCTCTTTTT | TTTTTTTTT | CTTTTTTTT | GGGCGAGGTG | GAGGCTTGCC | 3600 |
| CTGTTGCCCA | GGCTGGAGTG | CAGCGGCGCA | ATCTCGGTTC | ACTGCATCCT | CCACCTCCTG | 3660 |
| GGTCCAAATG | ATCCTCCTGC | CTTAGCTTCC | TGAGTAGGTG | GGATTACTGG | AACCCACCAC | 3720 |
| CACGCCCAGC | CAATTTTTAT | ATTTTTAGTA | GAGACGGGGT | TTCATGTTGG | CCAGGCTGGC | 3780 |
| CTCGAACTCC | TGACCTCGTG | ATCTGCCCGC | CTCAGCCTCC | CAATGTGCTA | GGATTACATG | 3840 |
| TGTGAGCCAC | TGCACCTGGC | CTCCGTGTGG | CTCTTTAAAG | CTCCACAATA | TTTTAGCATT | 3900 |
| CAGGTGCTCT | GTCATTTACT | TAACTATTTT | CTGATACACC | TCACACTGCG | ATTAACTTTC | 3960 |
| CTTATTTATC | TTTTTTATTA | TTTATTTATT | TATTTATTTG | AGACAGAGTC | TTGCTCTGTC | 4020 |
| ACCCAGGCTG | GAGTGCAGTG | GCACGATCTC | GGCTCACTGC | AACCTCTGCC | TCCCAGGTTC | 4080 |
| AAGTGATTCT | CCTGCCTCAG | CCTCCTGAGT | AGCTAGGATT | AGAGGCATGT | GCCACCACAC | 4140 |
| CTGGCTAATC | TTCGTATTTT | TAGCAGAGAT | GAGGTTTTAC | CATGTTGGTC | GGGCTGGTCG | 4200 |
| TGAACTCCTG | ACCTGGTGAT | CTGCCCACCT | CAGCCTCCCA | AAGTACTGGG | ATGACAGGCA | 4260 |
| TGAACCACTG | TGCCTGGCCA | TCTTTTTTAT | TTTTTAAAGA | GATGGGTTCT | GCTAAGTTGC | 4320 |
| CCAGGCTGGA | CCTGAACTCT | TGGGCTCAAG | TAATCTTCTC | ACCTAGTCTC | CTGGGTAGCT | 4380 |
| GCAACCAAAG | GCACCCGGTT | TATCTGCATT | CTCTTTTTT | TCTTTGAGAC | TGAGTCTTGC | 4440 |
| TCTGTAGCCC | AGGCTGGAGC | GCAGTGGCGT | GATCTCGGCT | CACTGCAACC | TCCGTCTTCA | 4500 |
| GGGTTCAAGC | AATTCTCCTG | CCTCAGCCTC | TGGAGTGGCT | GGGACTACAG | GCGTGTGCCA | 4560 |
| CCAGAGCGAG | TTAATTTTTT | TTTTTTTTG | TATTTTAGT | GGACACTGGG | TTTCACTATA | 4620 |
| TTGGCCAGGC | TGGTCTTGGA | CTCCTGACCT | CAAGTGATCC | GCCTGCCTTG | GCCTCCCAAA | 4680 |
| GTGCTGGGAT | TACAGGCACA | GGCGTGAGCC | ACTACACCTG | GCCTATCTGC | ATTCTCTTAA | 4740 |
| TAGTTTCTTA | GAAATGGATT | CTTAGGAGTA | GGATTACAGA | GTCAAGAGAC | ACAAGTTTTG | 4800 |
| TAGGCTGGGT | GCGGTGGCTC | ACGTCTGTGC | CTGTAATCCC | AGTACTTTAG | GAGGCCAAGG | 4860 |
| TGGGCAGATT | CATTGAGCTC | AGGAATTCGA | GACCAGCCTG | GCAACATGG | CAAAACCCCA | 4920 |
| TCTCTAAAGA | AATACAAAAA | TTAGCCAGGT | GTGGTGGTGT | GTGCCTGTAG | TCCTAGCTAC | 4980 |
| TTAGGAGGCT | GGGGTGGGAG | GATCAATTGA | GCCCAGGAGG | TTGAGACTGC | AGTGAGCTGT | 5040 |
| GATTGCACCA | TGGCACTCCA | GCCTGGGCCT | CAAAGTGAGA | TCCTGTCTCC | AAAACAAAAA | 5100 |
| AGATACAAGT | ATCCTTAAGG | CTCCTGCTAC | ACATGGCCAG | GAAGGTAGTC | TATTGGACAG | 5160 |
| TTTTAAGGTC | ATTATCAATA | TTAGCTCATT | TAATTCCCTC | CAAAACTCTG | TAAAGCACAT | 5220 |
| TCTGCTACCA | TAGTTGTCAT | ATTTTTGATG | GGGGAATCTA | CAGTGAGAGG | CAGTGCTGGG | 5280 |
| ATCTGAACCC | CATCTGGACA | GATTAGCTCC | AGGGCCCATG | CTCTTGACTG | GCTGGCCGCG | 5340 |
| CTGCCCACAC | TGAGTTGTTC | CTTCCTGGCA | GGGTAGGTGT | GCCTATCTCA | GGGACACTAG | 5400 |
| ACAGCTCCGA | GGGACCTCCC | TGTCCTTTTC | CTTTGTGAAC | TGTGTCACGT | TCTCCAGAGC | 5460 |

-continued

| | | | | | | |
|---|---|---|---|---|---|---|
| AGGGCTCAGA | CCTGCCCTGC | CTGCTCTGTG | CAGATGCCCT | TGGCCAAGGT | TTTCACACTG | 5520 |
| GAACAAGTTG | GTCCCTCCTC | CCCACCCCAG | CCTGTCCTTG | GCCCTCCTCC | AGGTCTCCTT | 5580 |
| CTGCATAGGA | GCAGCTCACC | CTGCCTCCTC | CAGAGTCCTG | CCCTAGAAGC | GCAATCCCTC | 5640 |
| TCCTTCCATC | CCCTGCCTGG | CTGCCTGGCT | CCTTCCCTCA | GCCTCCAAGA | CATGCTCAGT | 5700 |
| TTTCTTCCCT | CCTAAAACAC | CACCCACTGT | CTCATTTCCA | TTCATTTCTT | TCTTTCTTTC | 5760 |
| TTTCTTTTTT | TTTTTGAGA | GGGAGCCTCA | CTCTGTCACC | CAGGCTGAAG | TGCAGTGGCA | 5820 |
| TGATCTCCAC | TCACTGCAAC | CTCCGCCTCC | CAGGTTCAAG | CAATTCTCCT | GCCTCAGCCT | 5880 |
| CCTGAGTAGC | TGGGATTACA | GGCGCCTGCC | ACGATGCCCG | GCTAACTTTT | GTATTTTAG | 5940 |
| TAGAGACGGG | GTTTCGCCAT | GTTGGCCAGG | CTGGTCTCGA | GCTCCTGACC | TCAGGCAATC | 6000 |
| TGCCTGCCTC | AGCTTCCCAA | AGTGCTGGGA | TTACAGGTGT | GAGCCACCGC | GCCCACCCAT | 6060 |
| TCATTTCTCA | GTCCTTTGAA | TCTACTTGCC | CCTCCATCCC | GCCATGCCAC | CTACCCTAAC | 6120 |
| AACCTTCCCC | CTTAAACCTG | CGGGTTTGGC | CGGGCGCAGT | ACACTGAGTC | AGTACTGGTA | 6180 |
| CTGACCCAGG | TACCCCTCCA | GCCTCAGCTC | CAGTCAGATG | GGACAGCCTG | CTGGTCCCTG | 6240 |
| GCTGCTTCTG | CCCCCTCTTC | TGGAGCCCCA | GCCCTGGAGG | CTCCATGTGG | CTCAGCAGAA | 6300 |
| CTTCTTCTCC | TCCTGCTCTG | TGGTGGCCTC | TTGAGGGCAG | CACTCACCTT | GGAAAGCATG | 6360 |
| GAGTGTTTCA | ACCCTCACTG | CTCCCTGAAG | GACCAAGGTG | TCCCATTTTA | CAGTCGGGGG | 6420 |
| AGGAGGCACT | GTGATAAAGG | GGCTCTTCAG | ACCCACGTCT | GAGAGAGCCA | GGCTGCGCCG | 6480 |
| CCCCCGCGGC | CTTCCACCCT | TCACCGTCCA | GCCAGGGCCA | CTGCCATCAC | CGCCTGCTGG | 6540 |
| TCCTCACAGG | CGTCGGGGCC | CCAGGCAGTG | AGAAGGCGGC | TGCTGACTCC | TCTTTCCTCC | 6600 |
| CCAGCTGCCA | GGGACCTGGT | GAGCAAAGAG | GGCTTCCGGC | GGGCCCGGCA | CGTGGTGGGG | 6660 |
| GAGATTCGGC | GCACGGCCCA | GGCAGCGGCC | GCCCTGAGAC | GTGGCGACTA | CAGAGCCTTT | 6720 |
| GGCCGCCTCA | TGGTGGAGAG | CCACCGCTCA | CTCAGGTGAG | GCCCTCTGGG | CGCCCCGCTC | 6780 |
| CTGCCGGGCA | CAGGCCGGCC | CAGGCCCACC | CCTTCAATAT | CCTCTCTGCA | GAGACGACTA | 6840 |
| TGAGGTGAGC | TGCCCAGAGC | TGGACCAGCT | GGTGGAGGCT | GCGCTTGCTG | TGCCTGGGGT | 6900 |
| TTATGGCAGC | CGCATGACGG | GCGGTGGCTT | CGGTGGCTGC | ACGGTGACAC | TGCTGGAGGC | 6960 |
| CTCCGCTGCT | CCCCACGCCA | TGCGGCACAT | CCAGGTGGGC | GGGCACCAGG | GCCTGGGCGG | 7020 |
| GCAGGAGCGG | CAGCTTCCCG | GGGCCCTGCC | ACTCACCCCC | AGCCCGCCTC | TTACAGGAGC | 7080 |
| ACTACGGCGG | GACTGCCACC | TTCTACCTCT | CTCAAGCAGC | CGATGGAGCC | AAGGTGCTGT | 7140 |
| GCTTGTGAGG | CACCCCCAGG | ACAGCACACG | GTGAGGGTGC | GGGGCCTGCA | GGCCAGTCCC | 7200 |
| ACGGCTCTGT | GCCCGGTGCC | ATCTTCCATA | TCCGGGTGCT | CAATAAACTT | GTGCCTCCAA | 7260 |
| TGTGGTACCT | GCCTCCTCTA | GAGGTGGGTG | TATGCTTGGG | TGTCAGAGAA | TGGGGGATGT | 7320 |
| CAGAACCGCT | CCCCTACCCT | AGGGGAGCAC | CTCTCAGGCC | CCAGAAGAAT | GGGCAAGGCA | 7380 |
| GGGCCTAGCA | GTAGCAAAAC | CATTTATTAA | GTGCAGAACA | AAGGCTGGGT | CCTTGTGCTG | 7440 |
| CTCCAGCTC | TTTGGTTACA | AATAGGTTTG | GGCCCACAGA | GGACGGACCT | TGCCCCCTTC | 7500 |
| ATGCCTCCCA | GGAGACACCT | AGCCCCTGCT | CTGTGCATGC | GGGTGGGCTG | GGCCCCAGG | 7560 |
| GGTGCAAGGA | TGGAGTAGCT | GAGGAGGCTC | CGGGAGAGGA | GTCGGGAGGA | CGCCTAGTGG | 7620 |
| GACATTGCGG | GGGTGGCGCA | GGGTGCGGTC | AAGTTTGGAA | GAAACTGTTG | GGTCCA | 7676 |

( 2 ) INFORMATION FOR SEQ ID NO:8:

( i ) SEQUENCE CHARACTERISTICS:
( A ) LENGTH: 21 base pairs
( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

AGCCTTCCGG GAGGAGTTCG G  21

( 2 ) INFORMATION FOR SEQ ID NO:9:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

CTGGTTGTAG TCCGTGTGTT C  21

( 2 ) INFORMATION FOR SEQ ID NO:10:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

GCCAGCAGCT CCGCGACCTG G  21

( 2 ) INFORMATION FOR SEQ ID NO:11:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

GCTTCCTCCC TTCCAACGTG G  21

( 2 ) INFORMATION FOR SEQ ID NO:12:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

CCCAGGCTCC AGCGAGCGCT G  21

( 2 ) INFORMATION FOR SEQ ID NO:13:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

ACCTCTGAGG GTGCCGATGA G                        21

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CCCACAGCTC AGGGCAGAGT C                        21

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GGACACTTCT AATTGTCCTC C                        21

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GATGAACTGG TCCATGATGC C                        21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

AGGGGCACTG AGCTGACCAC C                        21

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CACTTCTACA CATTGGCGCC G                        21

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

CTTCGCAGGG ATGCCCTGTG G        21

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

TCATCACCAA CTCTAATGTC C        21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

TGTCAGCAGT GCCTATCTCT G        21

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

AGCAGCGGAG GCCTCCAGCA G        21

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

CCTCACCGTG TGCTGTCCTG G        21

( 2 ) INFORMATION FOR SEQ ID NO:24:

( i ) SEQUENCE CHARACTERISTICS:
        ( A ) LENGTH: 21 base pairs
        ( B ) TYPE: nucleic acid (C) STRANDEDNESS: single
        (D) TOPOLOGY: linear (i i) MOLECULE TYPE: DNA (genomic)

(x i) SEQUENCE DESCRIPTION: SEQ ID NO:24:

GGCTGCGCTT GCTGTGCCTG G 21

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:25:

CCTCACCGTG TGCTGTCCTG G 21

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:26:

CCTCACCGTG TGCTGTCCTG G 21

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:27:

GCGGGACTGC CACCTTCTAC C 21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:28:

CTCAATAAAC TTGTGCCTCC A 21

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:29:

CGGATATGGA AGATGGCACC GGG                                                                                    23

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:30:

AGAGCTGCAG GCGCGCGTCA TG                                                                                     22

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:31:

CCGAGCATCC CGCGCCGAC                                                                                          19

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:32:

CAGCTGCCCG CCCCACATCT                                                                                         20

(2) INFORMATION FOR SEQ ID NO:33:

(i) SEQUENCE CHARACTERISTICS:
        (A) LENGTH: 392 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:33:

```
Met Ala Ala Leu Arg Gln Pro Gln Val Ala Glu Leu Leu Ala Glu Ala
 1               5                  10                  15

Arg Arg Ala Phe Arg Glu Glu Phe Gly Ala Glu Pro Glu Leu Ala Val
             20                  25                  30

Ser Ala Pro Gly Arg Val Asn Leu Ile Gly Glu His Thr Asp Tyr Asn
             35                  40                  45

Gln Gly Leu Val Leu Pro Met Ala Leu Glu Leu Met Thr Val Leu Val
         50                  55                  60

Gly Ser Pro Arg Lys Asp Gly Leu Val Ser Leu Leu Thr Thr Ser Glu
 65                  70                  75                  80

Gly Ala Asp Glu Pro Gln Arg Leu Gln Phe Pro Leu Pro Thr Ala Gln
                 85                  90                  95
```

-continued

| | | | | | | | | | | | | | | |
|---|---|---|---|---|---|---|---|---|---|---|---|---|---|---|
| Arg | Ser | Leu | Glu 100 | Pro | Gly | Thr | Pro | Arg 105 | Trp | Ala | Asn | Tyr | Val 110 | Lys | Gly |
| Val | Ile | Gln 115 | Tyr | Tyr | Pro | Ala | Ala 120 | Pro | Leu | Pro | Gly | Phe 125 | Ser | Ala | Val |
| Val | Val 130 | Ser | Ser | Val | Pro | Leu 135 | Gly | Gly | Gly | Leu | Ser 140 | Ser | Ala | Ser |
| Leu 145 | Glu | Val | Ala | Thr | Tyr 150 | Thr | Phe | Leu | Gln | Gln 155 | Leu | Cys | Pro | Asp | Ser 160 |
| Gly | Thr | Ile | Ala | Ala 165 | Arg | Ala | Gln | Val | Cys 170 | Gln | Gln | Ala | Glu | His 175 | Ser |
| Phe | Ala | Gly | Met 180 | Pro | Cys | Gly | Ile | Met 185 | Asp | Gln | Phe | Ile | Ser 190 | Leu | Met |
| Gly | Gln | Lys 195 | Gly | His | Ala | Leu | Leu 200 | Ile | Asp | Cys | Arg | Ser 205 | Leu | Glu | Thr |
| Ser | Leu 210 | Val | Pro | Leu | Ser | Asp 215 | Pro | Lys | Leu | Ala | Val 220 | Leu | Ile | Thr | Asn |
| Ser 225 | Asn | Val | Arg | His | Ser 230 | Leu | Ala | Ser | Ser | Glu 235 | Tyr | Pro | Val | Arg | Arg 240 |
| Arg | Gln | Cys | Glu | Glu 245 | Val | Ala | Arg | Ala | Leu 250 | Gly | Lys | Glu | Ser | Leu 255 | Arg |
| Glu | Val | Gln | Leu 260 | Glu | Glu | Leu | Glu | Ala 265 | Ala | Arg | Asp | Leu | Val 270 | Ser | Lys |
| Glu | Gly | Phe 275 | Arg | Arg | Ala | Arg | His 280 | Val | Val | Gly | Glu | Ile 285 | Arg | Arg | Thr |
| Ala | Gln 290 | Ala | Ala | Ala | Ala | Leu 295 | Arg | Arg | Gly | Asp | Tyr 300 | Arg | Ala | Phe | Gly |
| Arg 305 | Leu | Met | Val | Glu | Ser 310 | His | Arg | Ser | Leu | Arg 315 | Asp | Asp | Tyr | Glu | Val 320 |
| Ser | Cys | Pro | Glu | Leu 325 | Asp | Gln | Leu | Val | Glu 330 | Ala | Ala | Leu | Ala | Val 335 | Pro |
| Gly | Val | Tyr | Gly 340 | Ser | Arg | Met | Thr | Gly 345 | Gly | Gly | Phe | Gly | Gly 350 | Cys | Thr |
| Val | Thr | Leu 355 | Leu | Glu | Ala | Ser | Ala 360 | Ala | Pro | His | Ala | Met 365 | Arg | His | Ile |
| Gln | Glu 370 | His | Tyr | Gly | Gly | Thr 375 | Ala | Thr | Phe | Tyr | Leu 380 | Ser | Gln | Ala | Ala |
| Asp 385 | Gly | Ala | Lys | Val | Leu 390 | Cys | Leu | | | | | | | | |